(12) United States Patent
Levy et al.

(10) Patent No.: US 9,090,943 B2
(45) Date of Patent: Jul. 28, 2015

(54) METHODS FOR DETECTING AN INCREASED SUSCEPTIBILITY TO CANCER

(75) Inventors: Asaf Levy, Nes Ziona (IL); Eitan Freidman, Tel Aviv (IL)

(73) Assignees: Rosetta Genomics Ltd., Rehovot (IL); Tel Hashomer Medical Research Infrastructure and Services Ltd., Ramat Gan (IL)

( * ) Notice: Subject to any disclaimer, the term of this patent is extended or adjusted under 35 U.S.C. 154(b) by 185 days.

(21) Appl. No.: 13/131,727

(22) PCT Filed: Nov. 30, 2009

(86) PCT No.: PCT/IL2009/001127
§ 371 (c)(1),
(2), (4) Date: May 27, 2011

(87) PCT Pub. No.: WO2010/061396
PCT Pub. Date: Jun. 3, 2010

(65) Prior Publication Data
US 2011/0229894 A1  Sep. 22, 2011

Related U.S. Application Data

(60) Provisional application No. 61/118,614, filed on Nov. 30, 2008.

(51) Int. Cl.
*C07H 21/04* (2006.01)
*C12Q 1/68* (2006.01)

(52) U.S. Cl.
CPC ........ *C12Q 1/6886* (2013.01); *C12Q 2600/112* (2013.01); *C12Q 2600/118* (2013.01); *C12Q 2600/178* (2013.01)

(58) Field of Classification Search
None
See application file for complete search history.

(56) References Cited

U.S. PATENT DOCUMENTS

2003/0092019 A1 * 5/2003 Meyer et al. .............. 435/6
2008/0261908 A1   10/2008 Croce et al.

OTHER PUBLICATIONS

NCBI rs11169571, Nov. 17, 2003.*
Satagopan et al. (Cancer, Epidemiology, Biomarkers and Prevention, vol. 10, pp. 467-473, May 2001).*
Shen et al. (Int. J. Cancer, vol. 124, pp. 1178-1182, 2009).*
Shen et al. (Carcinogenesis, vol. 29, No. 10, pp. 1963-1966, 2008).*
Lucentini (The Scientist; 2004, vol. 24, p. 20).*
Hirschhorn et al. (Genetics in Medicine. vol. 4, No. 2, pp. 45-61, Mar. 2002).*
Ioannidis (Nature Genetics, vol. 29, pp. 306-309, Nov. 2001).*
Nastiuk et al (Prostates, vol. 40, No. 3, pp. 172-177, 1999) t.*
Wu et al. (Carcinogenesis, vol. 29, No. 9, pp. 1710-1716, Mar. 2008).*
Kontorovich et al. (Int. J. Cancer, vol. 127, pp. 589-597, 2009).*
Sung et al. (Cancer Epidemiol Biomarkers, "Common genetic variants in the microRNA biogenesis pathway are not associated with breast cancer risk in Asian women" Jun. 2012).*
Bhatti et al., "Candidate Single Nucleotide Polymorphism Selection using Publicly Available Tools: A Guide for Epidemiologists," American Journal of Epidemiology, 2006, vol. 164, No. 8, pp. 794-804.
Chen et al., "Allelic imbalance in BRCA1 and BRCA2 gene expression is associated with an increased breast cancer risk," Human Molecular Genetics, 2008, vol. 17, No. 9, pp. 1336-1348.
International Search Report for International Application No. PCT/IL09/01127 mailed Mar. 19, 2010, 1 page.

* cited by examiner

*Primary Examiner* — Jeanine A Goldberg
(74) *Attorney, Agent, or Firm* — Polsinelli PC; Ron Galant

(57) ABSTRACT

The invention relates to methods for detecting an altered susceptibility to breast and ovarian cancer in a subject carrying a BRCA mutation, comprising determining the nucleic acid sequence of a polymorphism of a microRNA-related gene.

6 Claims, 15 Drawing Sheets

METHODS FOR DETECTING AN INCREASED SUSCEPTIBILITY TO CANCER

CROSS-REFERENCE TO RELATED PATENT APPLICATIONS

This application is the U.S. National Phase of PCT/IL2009/001127, filed Nov. 30, 2009, which claims priority from U.S. Provisional Application No. 61/118,614, filed Nov. 30, 2008, which are incorporated herein by reference in entirety.

FIELD OF THE INVENTION

The invention relates to methods for detecting an increased susceptibility to breast and ovarian cancer in a subject carrying a BRCA mutation, comprising determining the nucleic acid sequence of a polymorphism of a microRNA-related gene.

BACKGROUND OF THE INVENTION

The lifetime risk for developing invasive breast cancer in the Western world is about 12%, and 1 in 33 women will die of breast cancer (Pharoah et al., The Breast. 1998; 7:255-259). Epithelial ovarian cancer (EOC) is the fifth leading cause of cancer-related deaths in women in the United States and the leading cause of gynecologic cancer-related deaths (Jemal A, Siegel et al., Cancer Statistics, 2007). Most breast cancer cases are sporadic, with no family history of cancer. In up to 10% of breast cancer cases a family history can be elicited, and in a subset of these individuals, germline mutations can be detected, primarily in either the BRCA1 or BRCA2 genes.

Carriers of germline BRCA1 (MIM #113705) or BRCA2 (MIM #600185) gene mutations are clearly at an increased risk for developing breast and ovarian cancer, with an estimated lifetime risk of ~80% for developing breast cancer and ~50% for ovarian cancer, rates that are 6-7- and 30-fold increased, respectively, over those of the general population (Wacholder et al., Science 2004; 306:2187-2191). The risk of breast cancer increases with age. A woman in the general population faces about a 12% lifetime risk of developing breast cancer. This risk remains low before age 50; the majority of risk occurs after age 60. Women with a BRCA1 or BRCA2 mutation have a much higher lifetime risk for breast cancer, and much of the risk occurs at a younger age.

There is substantial variability in the penetrance of breast cancer in BRCA1/2 mutation carriers, even among carriers of an identical mutation within families. These different penetrance rates, combined with the variability in age at diagnosis in affected mutation carriers, may imply that modifier factors—genetic and environmental—are operative in BRCA1/2 carriers to affect penetrance. Over the years, a host of environmental and genetic factors have been evaluated as putative modifiers of BRCA1/2 mutations: environmental exposures (e.g., irradiation), personal habits (e.g., smoking), lifestyle (e.g., involvement in sports), reproductive factors (e.g., age at first menstrual period), as well as the action of additional so-called "modifier genes" (e.g., a single SNP in the RAD51 gene). Despite substantial and extensive studies, few factors have emerged as "true modifiers" by virtue of reproducibility and independent validation.

Modification of breast cancer risk in BRCA1/2 mutation carriers by other genes have been proposed and investigated. Such an evaluation involves a case-control study design that determines the rates of either known functional polymorphisms or single nucleotide polymorphisms (SNPs) within and around candidate genes and compares these rates between affected and unaffected BRCA gene mutation carriers. The putative role that aberrant gene silencing by miRNA plays in affecting mutant BRCA allele penetrance has not been studied.

MicroRNAs (miRNAs, miRs) are single-stranded RNA molecules of about 21-23 nucleotides in length thought to regulate the expression of other genes. miRNAs are encoded by genes that are transcribed from DNA but not translated into protein. miRNAs are first transcribed as pri-miRNA and are subsequently processed to short stem-loop structures, pre-miRNA, in the cell nucleus. These pre-miRNAs are then processed to mature miRNAs in the cytoplasm by interaction with the endonuclease Dicer, which also initiates the formation of the RNA-induced silencing complex (RISC).

In order to function in gene regulation, a miRNA is complementary to a part of one or more mRNAs. The miRNA with the complex RISC is guided to target sequences located at the 3'-terminal untranslated regions (3'-UTRs) of mRNAs by base pairing. Annealing of miRNA to mRNA inhibits protein translation by cleavage of the mRNA through a process similar to RNA interference (RNAi), or by blocking the protein translation machinery without causing the mRNA to be degraded (Meister and Tuschl, Nature 2004; 431:343-349). Accumulating evidence has revealed that 7 nt at the 5'-terminus of an miRNA, from position 2 to position 8, called the 'seed' region, are essential for their function (Brennecke et al., PLoS Biol 2005; 3:e85).

MicroRNA regulation has a major impact on the proper regulation of a cell, in particular, cellular proliferation and differentiation. There is evidence that the expression level of several genes and proteins in tumors is also partially regulated by miRNA. Let-7, targeting the oncogene RAS, is down-regulated in lung cancers (Takamizawa et al., Cancer Res 2004; 64:3753-3756). Furthermore, a germline mutation in the pri-miR-16-1/15a precursor was found to cause its reduced transcription in a patient with familial CLL (Calin et al., N Engl J Med 2005; 353:1793-1801).

A SNP located in the miRNA-binding site of a miRNA target may disrupt miRNA-target interaction, resulting in the deregulation of target gene expression. Such SNP-associated deregulation of the expression of an oncogene or tumor suppressor gene might contribute to tumorigenesis. In this hypothetical model, aberrant miRNA binding, affect gene expression patterns in a way that abrogates their ability to fulfill their designated biological role as translation regulators. Such an effect may hypothetically modify cancer risk in BRCA1 and BRCA2 mutation carriers. This putative involvement of miRNA in modifying cancer risk can be detected by analysis of SNPs in miRNA binding sites and/or miRNA precursors.

There is an unmet need for detecting increased susceptibility to breast and ovarian cancer in subjects carrying a BRCA mutation, so that more accurate risk assessment becomes possible. Such information could have significant implications in terms of genetic counseling.

SUMMARY OF THE INVENTION

The present invention provides a method for detecting an altered susceptibility to a cancer in a subject carrying a BRCA mutation, comprising determining the nucleic acid sequence of a polymorphism of a microRNA-related gene or variant thereof, wherein the presence of a specific variation in said microRNA-related gene or variant thereof is indicative of the risk of developing said cancer in said subject.

According to one embodiment the cancer is selected from breast and ovarian cancer. According to another embodiment the BRCA mutation is selected from BRCA1 and BRCA2. According to yet another embodiment the microRNA-related gene is selected from the group consisting of genes encoding a microRNA, a microRNA precursor, a mature miRNA and a microRNA target gene; and a gene involved in microRNA processing. According to some embodiments the variation in the microRNA-related gene is in a microRNA binding site within the 3' UTR of a microRNA target gene. According to another embodiment, the microRNA-related gene or variant thereof is selected from the group consisting of SEQ ID NOS: 92-96, 103, 1, 8, 9, 23, 25, 2-7, 10-22, 24, 90, 104, 105, 132, 91, 98-102, 106 and 107.

In one embodiment, of the invention the microRNA-related gene or variant thereof comprises SEQ ID NOS: 92-94, and the presence of cytosine (C) at the 1071738 SNP is indicative of a decreased risk for developing said cancer in said subject. In another embodiment of the invention the microRNA-related gene or variant thereof comprises SEQ ID NOS: 95-96, and the presence of adenosine (A) at the rs1621 SNP is indicative of an increased risk for developing said cancer in said subject. In another embodiment of the invention the microRNA-related gene or variant thereof comprises SEQ ID NO: 103, and the presence of thymidine (T) at the rs2747648 SNP is indicative of a decreased risk for developing said cancer in said subject. In another embodiment of the invention the microRNA-related gene or variant thereof comprises SEQ ID NO: 9, and the presence of adenosine (A) at the rs3842753 SNP is indicative of a decreased risk for developing said cancer in said subject. In another embodiment of the invention the microRNA-related gene or variant thereof comprises SEQ ID NO: 23, and the presence of adenosine (A) at the rs6505162 SNP is indicative of a decreased risk for developing said cancer in said subject. In another embodiment of the invention the microRNA-related gene or variant thereof comprises SEQ ID NO: 1, and the presence of cytosine (C) at the rs11169571 SNP is indicative of an increased risk for developing said cancer in said subject. In another embodiment of the invention the microRNA-related gene or variant thereof comprises SEQ ID NO: 8, and the presence of cytosine (C) at the rs3626 SNP is indicative of an increased risk for developing said cancer in said subject. In another embodiment of the invention the microRNA-related gene or variant thereof comprises SEQ ID NO: 25, and the presence of thymidine (T) at the rs895819 SNP is indicative of an increased risk for developing said cancer in said subject. In another embodiment of the invention the microRNA-related gene or variant thereof comprises SEQ ID NO: 91, and the presence of guanosine (G) at the rs1056930 SNP is indicative of a decreased risk for developing said cancer in said subject. In another embodiment of the invention the microRNA-related gene or variant thereof comprises SEQ ID NO: 104, and the presence of adenosine (A) at the rs28674628 SNP is indicative of a decreased risk for developing said cancer in said subject. In another embodiment of the invention the microRNA-related gene or variant thereof comprises SEQ ID NO: 90, and the presence of thymidine (T) at the rs1042992 SNP is indicative of a decreased risk for developing said cancer in said subject. In another embodiment of the invention the microRNA-related gene or variant thereof comprises SEQ ID NO: 98, and the presence of cytosine (C) at the rs3763763 SNP is indicative of a decreased risk for developing said cancer in said subject. In another embodiment of the invention the microRNA-related gene or variant thereof comprises SEQ ID NOS: 99-100, and the presence of thymidine (T) at the rs7085 SNP is indicative of a decreased risk for developing said cancer in said subject. In another embodiment of the invention the microRNA-related gene or variant thereof comprises SEQ ID NO: 101, and the presence of adenosine (A) at the rs868 SNP is indicative of an increased risk for developing said cancer in said subject. In another embodiment of the invention the microRNA-related gene or variant thereof comprises SEQ ID NO: 102, and the presence of thymidine (T) at the rs2289047 SNP is indicative of an increased risk for developing said cancer in said subject. In another embodiment of the invention the microRNA-related gene or variant thereof comprises SEQ ID NO: 105, and the presence of guanosine (G) at the rs35664313 SNP is indicative of an increased risk for developing said cancer in said subject. In another embodiment of the invention the microRNA-related gene or variant thereof comprises SEQ ID NO: 106-107, and the presence of guanosine (G) at the rs8176318 SNP is indicative of a decreased risk for developing said cancer in said subject. In another embodiment of the invention the microRNA-related gene or variant thereof comprises SEQ ID NO: 132, and the presence of cytosine (C) at the rs2910164 SNP is indicative of a decreased risk for developing said cancer in said subject. In another embodiment of the invention the microRNA-related gene or variant thereof comprises SEQ ID NO: 132, and the presence of guanosine (G) at the rs2910164 SNP is indicative of a decreased risk for developing said cancer in said subject.

In some embodiments the nucleic acid sequence is determined by a method comprising nucleic acid amplification. In some embodiments, the amplification method is real-time PCR. In some embodiments, the amplification method comprises the use of a primer selected from the group consisting of SEQ ID NOS: 26-57. In some embodiments, the primer is a forward primer selected from the group consisting of SEQ ID NOS: 26-41. In some embodiments, the primer is a reverse primer selected from the group consisting of SEQ ID NOS: 42-57. In additional embodiments the nucleic acid sequence is determined by a method comprising nucleic acid extension. In some embodiments, the extension method comprises a primer selected from the group consisting of SEQ ID NOS: 58-89.

In some embodiments the subject is a heterozygote for the specific variation, and in other embodiments the subject is a homozygote for the specific variation. In some embodiments, the microRNA-related gene or variant thereof comprises SEQ ID NO: 104, and heterozygosity at the rs28674628 SNP is indicative of an increased risk of developing breast or ovarian cancer in a subject carrying a BRCA mutation. In some embodiments, the microRNA-related gene or variant thereof comprises SEQ ID NO: 25, and heterozygosity at the rs895819 SNP is indicative of a decreased risk of developing breast or ovarian cancer in a subject carrying a BRCA mutation.

In another aspect of the invention a kit is provided for detecting a risk of developing cancer in a subject carrying a BRCA mutation, comprising means for determining the nucleic acid sequence of a polymorphism of a microRNA-related gene or variant thereof, wherein the presence of a specific variation in said microRNA-related gene or variant thereof is indicative of the risk of developing said cancer in said subject. In some embodiments, the kit is for detecting a risk of developing cancer in a subject carrying the BRCA1 mutation, while in other embodiments, the subject carries the BRCA2 mutation. In some embodiments, said microRNA-related gene is selected from the group comprising genes encoding a microRNA, a microRNA precursor and a microRNA target gene, and a gene involved in microRNA processing. In some embodiments, said microRNA-related gene or variant thereof is selected from the group consisting of SEQ ID NOS: 92-96, 103, 1, 8, 9, 23, 25, 2-7, 10-22, 24, 90, 104, 105, 132, 91, 98-102, 106 and 107. In some embodiments, said nucleic acid sequence is determined by a method comprising nucleic acid amplification. In some embodiments, the nucleic acid amplification method is real-time PCR. In some embodiments, said amplification method comprises use of a primer selected from the group consisting of SEQ ID NOS: 26-57. In some embodiments, the primer is a forward primer selected from the group consisting of SEQ ID NOS: 26-41. In some embodiments, the primer is a reverse primer selected from the group consisting of SEQ ID NOS: 42-57. In some embodiments, said nucleic acid sequence is determined by a method comprising nucleic acid extension. In some embodiments, the nucleic acid extension method comprises use of a primer selected from the group consisting of SEQ ID NOS: 58-89.

BRIEF DESCRIPTION OF THE DRAWINGS

FIG. 1A presents the age-dependent development of ovarian cancer in BRCA1 carriers bearing the following genotypes at the rs3842753 SNP (in SEQ ID NO: 9): AA homozygote-bold curve, CC homozygote-dashed curve and AC heterozygote-dotted curve.

FIG. 1B presents the age-dependent development of breast cancer in BRCA2 carriers bearing the following genotypes at the rs6505162 SNP (in SEQ ID NO: 23): AA homozygote-bold curve, CC homozygote-dashed curve and AC heterozygote-dotted curve.

FIG. 1C presents the age-dependent development of breast or ovarian cancer in BRCA2 carriers bearing the following genotypes at the rs11169571 SNP (in SEQ ID NO: 1): TT homozygote-dashed curve, CC homozygote-bold curve and CT heterozygote-dotted curve.

FIG. 1D presents the age-dependent development of ovarian cancer in the combined group of BRCA1 and BRCA2 carriers, bearing the following genotypes at the rs3626 SNP (in SEQ ID NO: 8): GG homozygote-dashed curve, CC homozygote-bold curve and CG heterozygote-dotted curve.

FIG. 1E presents the age-dependent development of breast or ovarian cancer in BRCA2 carriers bearing the following genotypes at the rs895819 SNP (in SEQ ID NO: 25): TT homozygote-bold curve, CC homozygote-dashed curve and CT heterozygote-dotted curve.

FIG. 3A presents the age-dependent development of both breast and ovarian cancer in BRCA1 carriers bearing the following genotypes at the rs1071738 SNP (in SEQ ID NO: 92-94): GG homozygote-solid curve, GC heterozygote-dashed curve and CC homozygote-dotted curve.

FIG. 3B presents the age-dependent development of ovarian cancer in BRCA1 carriers, bearing the following genotypes at the rs2747648 SNP (in SEQ ID NO: 103): TT homozygote-solid curve and CT heterozygote-dashed curve.

FIG. 3C presents the age-dependent development of breast cancer in BRCA2 carriers, bearing the following genotypes at the rs2747648 SNP (in SEQ ID NO: 103): TT homozygote-solid curve and CT heterozygote-dashed curve.

FIG. 3D presents the age-dependent development of breast cancer in BRCA1 carriers, bearing the following genotypes at the rs28674628 SNP (in SEQ ID NO: 104): AA homozygote-solid curve, GA heterozygote-dashed curve and GG homozygote-dotted curve.

FIG. 3E presents the age-dependent development of ovarian cancer in BRCA1 carriers, bearing the following genotypes at the rs2910164 SNP (in SEQ ID NO: 132): GG homozygote-solid curve, CG heterozygote-dashed curve and CC homozygote-dotted curve.

FIG. 3F presents the age-dependent development of breast cancer in BRCA2 carriers, bearing the following genotypes at the rs2910164 SNP (in SEQ ID NO: 132): GG homozygote-solid curve, CG heterozygote-dashed curve and CC homozygote-dotted curve.

FIG. 3G presents the age-dependent development of ovarian cancer in the combined group of BRCA1 and BRCA2 carriers, bearing the following genotypes at the rs35664313 SNP (in SEQ ID NO: 105): GG homozygote-solid curve, G.DEL heterozygote-dashed curve and DEL.DEL homozygote-dotted curve.

FIG. 3H presents the age-dependent development of ovarian cancer in BRCA2 carriers, bearing the following genotypes at the rs35664313 SNP (in SEQ ID NO: 105): GG homozygote-solid curve, G.DEL heterozygote-dashed curve and DEL.DEL homozygote-dotted curve.

FIG. 3I presents the age-dependent development of ovarian cancer in BRCA2 carriers bearing the following genotypes at the rs895819 SNP (in SEQ ID NO: 25): TT homozygote-solid curve, CT heterozygote-dashed curve and CC homozygote-dotted curve.

DETAILED DESCRIPTION

Figure 1A:
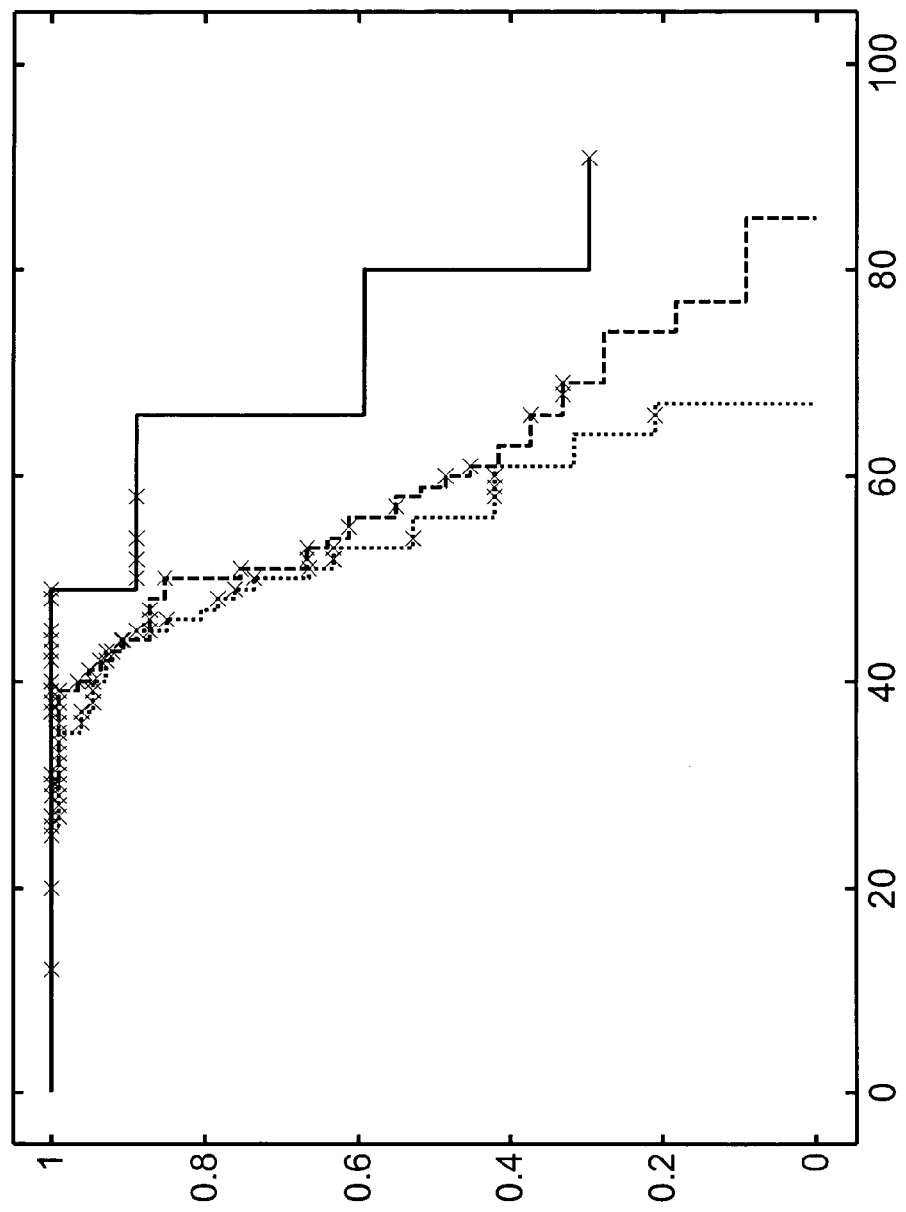
FIGS. 1A-1E are Kaplan-Meier plots depicting the age-dependent development of breast or ovarian cancer in BRCA1 and/or BRCA2 carriers. The y-axis represents the fraction of subjects who developed cancer and the x-axis represents the age of the subjects (in years). Each drop in the curve represents a subject diagnosed with breast or ovarian cancer. Cross symbols represent censored subjects, who were not diagnosed with cancer at the depicted age.

Methods are provided for detecting an altered susceptibility to breast or ovarian cancer in a subject carrying a BRCA mutation comprising determining the nucleic acid sequence of a polymorphism of a microRNA-related gene. Other aspects of the invention will become apparent to the skilled artisan by the following description of the invention.

Before the present compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

A. Definitions a. About

As used herein, the term "about" refers to +/−10%.

b. Allele

As used herein, allele is one of the variant forms of a gene at a particular locus on a chromosome. Different alleles produce variation in inherited characteristics. In an individual, one form of the allele (the dominant one) may be expressed more than another form (the recessive one). When "genes" are considered simply as segments of a nucleotide sequence, allele refers to each of the possible alternative nucleotides at a specific position in the sequence. For example, a CT polymorphism such as CCT[C/T]CCAT would have two alleles: C and T.

c. Antisense

The term "antisense," as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated.

d. Attached

"Attached" or "immobilized", as used herein to refer to a probe and a solid support, may mean that the binding between the probe and the solid support is sufficient to be stable under conditions of binding, washing, analysis, and removal. The binding may be covalent or non-covalent. Covalent bonds may be formed directly between the probe and the solid support or may be formed by a cross linker or by inclusion of a specific reactive group on either the solid support or the probe or both molecules. Non-covalent binding may be one or more of electrostatic, hydrophilic, and hydrophobic interactions. Included in non-covalent binding is the covalent attachment of a molecule, such as streptavidin, to the support and the non-covalent binding of a biotinylated probe to the streptavidin. Immobilization may also involve a combination of covalent and non-covalent interactions.

e. Biological Sample

"Biological sample", as used herein, means a sample of biological tissue or fluid that comprises nucleic acids. Such samples include, but are not limited to, tissue or fluid isolated from subjects. Biological samples may also include sections of tissues such as biopsy and autopsy samples, FFPE samples, frozen sections taken for histological purposes, blood, plasma, serum, sputum, stool, tears, mucus, effusions, amniotic fluid, ascetic fluid, hair and skin. Biological samples also include explants and primary and/or transformed cell cultures derived from animal or patient tissues.

Biological samples may also be blood, a blood fraction, urine, effusions, ascitic fluid, saliva, cerebrospinal fluid, cervical secretions, vaginal secretions, endometrial secretions, gastrointestinal secretions, bronchial secretions, sputum, cell line, tissue sample, cellular content of fine needle aspiration (FNA) or secretions from the breast. A biological sample may be provided by removing a sample of cells from an animal, but can also be accomplished by using previously isolated cells (e.g., isolated by another person, at another time, and/or for another purpose), or by performing the methods described herein in vivo. A biological sample may also be a surgically removed sample, and a sample obtained by tissue-sampling procedures such as laparoscopic methods. Archival tissues, such as those having treatment or outcome history, may also be used.

f. Cancer Prognosis

A forecast or prediction of the probable course or outcome of the cancer and response to its treatment. As used herein, cancer prognosis includes distinguishing between cancer stages and subtypes, and the forecast or prediction of any one or more of the following: duration of survival of a patient susceptible to or diagnosed with a cancer, duration of recurrence-free survival, duration of progression-free survival of a patient susceptible to or diagnosed with a cancer, response rate in a group of patients susceptible to or diagnosed with a cancer, duration of response in a patient or a group of patients susceptible to or diagnosed with a cancer, and/or likelihood of metastasis in a patient susceptible to or diagnosed with a cancer. As used herein, "prognostic for cancer" means providing a forecast or prediction of the probable course or outcome of the cancer. In some embodiments, "prognostic for cancer" comprises providing the forecast or prediction of (prognostic for) any one or more of the following: duration of survival of a patient susceptible to or diagnosed with a cancer, duration of recurrence-free survival, duration of progression free survival of a patient susceptible to or diagnosed with a cancer, response rate in a group of patients susceptible to or diagnosed with a cancer, duration of response in a patient or a group of patients susceptible to or diagnosed with a cancer, and/or likelihood of metastasis in a patient susceptible to or diagnosed with a cancer.

g. Complement

"Complement" or "complementary", as used herein to refer to a nucleic acid, may mean Watson-Crick (e.g., A-T/U and C-G) or Hoogsteen base pairing between nucleotides or nucleotide analogs of nucleic acid molecules. A full complement or fully complementary may mean 100% complementary base pairing between nucleotides or nucleotide analogs of nucleic acid molecules. C-G pairing may occur in RNA secondary structures (such as miR precursors) and in miR-target association. In some embodiments, the complementary sequence has a reverse orientation (5'-3').

h. Detection

"Detection" means detecting the presence of a component in a sample. Detection also means detecting the absence of a component. Detection also means measuring the level of a component, either quantitatively or qualitatively. Detection also means identifying or diagnosing cancer in a subject. "Early detection" means identifying or diagnosing cancer in a subject at an early stage of the disease, especially before it causes symptoms.

i. Fragment

"Fragment" is used herein to indicate a non-full-length part of a nucleic acid or polypeptide. Thus, a fragment is itself also a nucleic acid or polypeptide, respectively.

j. Gene

"Gene", as used herein, may be a natural (e.g., genomic) or synthetic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA or antisense RNA. A gene may also be an mRNA or cDNA corresponding to the coding regions (e.g., exons and miRNA) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto.

k. Identity

"Identical" or "identity", as used herein in the context of two or more nucleic acids or polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

l. Inhibit

"Inhibit", as used herein, may mean prevent, suppress, repress, reduce or eliminate.

m. Label

"Label", as used herein, may mean a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and other entities which can be made detectable. A label may be incorporated into nucleic acids and proteins at any position.

n. Metastasis

"Metastasis", as used herein, means the process by which cancer spreads from the place at which it first arose as a primary tumor to other locations in the body. The metastatic progression of a primary tumor reflects multiple stages, including dissociation from neighboring primary tumor cells, survival in the circulation, and growth in a secondary location.

o. MicroRNA

"MicroRNAs" (miRNAs, miRs), as used herein, are a group of about 22-oligonucleotide-long noncoding RNA molecules involved in post-transcriptional gene regulation, that act by binding to a complementary binding site in the 3'UTR of specific mRNA molecules, thereby leading to either suppression of translation or cleavage of the mRNA. The "seed" or "seed region" refers to the six-seven nucleotides at positions 2-8 of the 5' region of a miRNA, whose complementarity to the binding site on the target mRNA largely influences binding effectiveness.

The designation of miRs herein is in accordance with the miRBase registry name (release 13.0).

p. MicroRNA-Related Gene

As used herein, "microRNA-related genes" include genes encoding microRNA and microRNA precursors, genes of whose transcripts are involved in microRNA processing, and genes which encode transcripts to which microRNAs bind (microRNA target genes).

q. MicroRNA Binding Site

As used herein, a microRNA binding site is the region complementary to the miR seed. This may be a predicted region according to publicly available algorithms.

r. Mismatch

"Mismatch" means a nucleobase of a first nucleic acid that is not capable of pairing with a nucleobase at a corresponding position of a second nucleic acid.

s. Nucleic Acid

"Nucleic acid" or "oligonucleotide" or "polynucleotide", as used herein, may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single-stranded or double-stranded, or may contain portions of both double-stranded and single-stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog may be located, for example, at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e., ribonucleotides, containing a non-naturally occurring nucleobase instead of a naturally occurring nucleobase such as uridine or cytidine modified at the 5-position, e.g., 5-(2-amino)propyl uridine, 5-bromo uridine; adenosine and guanosine modified at the 8-position, e.g., 8-bromo guanosine; deaza nucleotides, e.g., 7-deaza-adenosine; O- and N-alkylated nucleotides, e.g., N6-methyl adenosine are suitable. The 2'-OH-group may be replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. Modified nucleotides also include nucleotides conjugated with cholesterol through, e.g., a hydroxyprolinol linkage as described in Krutzfeldt et al., Nature 2005; 438:685-689, Soutschek et al., Nature 2004; 432:173-178, and U.S. Patent Publication No. 20050107325, which are incorporated herein by reference. Additional modified nucleotides and nucleic acids are described in U.S. Patent Publication No. 20050182005, which is incorporated herein by reference. Modifications of the ribose-phosphate backbone may be done for a variety of reasons, e.g., to increase the stability and half-life of such molecules in physiological environments, to enhance diffusion across cell membranes, or as probes on a biochip. The backbone modification may also enhance resistance to degradation, such as in the harsh endocytic environment of cells. The backbone modification may also reduce nucleic acid clearance by hepatocytes, such as in the liver and kidney. Mixtures of naturally occurring nucleic acids and analogs may be made; alternatively, mixtures of different nucleic acid analogs, and mixtures of naturally occurring nucleic acids and analogs may be made.

t. Penetrance

"Penetrance", as used herein, describes the proportion of individuals carrying a particular variation of an allele that also express a particular phenotype. Accordingly, penetrance is the percentage of individuals with a specific genotype that possess an associated phenotype.

u. Polymorphism

"Polymorphism", as used herein, may mean a difference in DNA sequence among individuals, such as the occurrence of two or more alleles at a locus in a population. The term may be applied to many situations ranging from genetic traits or disorders in a population to the variation in the sequence of DNA or proteins. Polymorphism may provide for diversity among the members of a population, by introducing variation in alleles among members of the same species. Specific variations within a population may be associated with certain diseases or may be indicative of a particular disease outcome.

v. Probe

"Probe", as used herein, may mean an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind.

w. Promoter

"Promoter", as used herein, may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

x. Single Nucleotide Polymorphism (SNP)

SNP, as used herein, refers to an allelic variation which is defined by two alternative bases found at a specific and particular nucleotide in coding and in non-coding genomic DNA. For example, a CT SNP such as CCT[C/T]CCAT would have two allelic variations: C and T.

y. Stage of Cancer

As used herein, the term "stage of cancer" refers to a numerical measurement of the level of advancement of a cancer. Criteria used to determine the stage of a cancer include, but are not limited to, the size of the tumor, whether the tumor has spread to other parts of the body and where the cancer has spread (e.g., within the same organ or region of the body or to another organ).

z. Stringent Hybridization Conditions

"Stringent hybridization conditions", as used herein, may mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5-10° C. lower than the thermal melting point for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

aa. Subject

As used herein, the term "subject" refers to a mammal, including both human and other mammals. The methods of the present invention are preferably applied to human subjects.

bb. Substantially Complementary

"Substantially complementary", as used herein, may mean that a first sequence is at least 60%-99% identical to the complement of a second sequence over a region of 8-50 or more nucleotides, or that the two sequences hybridize under stringent hybridization conditions.

cc. Substantially Identical

"Substantially identical", as used herein, may mean that a first and second sequence are at least 60%-99% identical over a region of 8-50 or more nucleotides or amino acids, or with respect to nucleic acids, if the first sequence is substantially complementary to the complement of the second sequence.

dd. Treat

"Treat" or "treating", as used herein when referring to protection of a subject from a condition, may mean preventing, suppressing, repressing, or eliminating the condition. Preventing the condition involves administering a composition described herein to a subject prior to onset of the condition. Suppressing the condition involves administering the composition to a subject after induction of the condition but before its clinical appearance. Repressing the condition involves administering the composition to a subject after clinical appearance of the condition such that the condition is reduced or prevented from worsening. Elimination of the condition involves administering the composition to a subject after clinical appearance of the condition such that the subject no longer suffers from the condition.

ee. Tumor

"Tumor", as used herein, refers to all neoplastic cell growth and proliferation, whether malignant or benign, and all precancerous and cancerous cells and tissues.

ff. Variant

"Variant", used herein to refer to a nucleic acid, may mean (i) a portion of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

gg. Vector

"Vector" used herein may mean a nucleic acid sequence containing an origin of replication. A vector may be a plasmid, a bacteriophage, a bacterial artificial chromosome or a yeast artificial chromosome. A vector may be a DNA or RNA vector. A vector may be either a self-replicating extrachromosomal vector or a vector which integrates into a host genome.

B. BRCA Mutation and Breast/Ovarian Cancer Susceptibility

"BRCA", or "breast cancer gene", is one of several genetic mutations linked to breast cancer and ovarian cancer. Mutations in BRCA1 or BRCA2 predispose to breast cancer and ovarian cancer. The risk of developing cancer that is associated with a BRCA1 or BRCA2 cancer-predisposing mutation is not known and appears to be variable even within families of similar ethnic background with the same mutation. About 5%40% of women in whom breast or ovarian cancer is diagnosed have a hereditary form of cancer predominantly due to germline mutations in the BRCA1 or BRCA2 genes (National Cancer Institute, National Institutes of Health: Genetics of Breast and Ovarian Cancer (PDQ)). Women with BRCA mutations who have no family history of breast cancer are still at increased risk for the disease, a risk simply attributable to being a mutation carrier. Their risk is believed to be comparable to families with a history of breast cancer and the same mutation. Prognosis for individuals with BRCA1 or BRCA2 cancer-predisposing mutations may not be different from that of similarly affected individuals who do not harbor the mutation (=controls) (Rennert G et al., N Engl J Med 2007; 357(2):115-23).

Molecular genetic testing for BRCA1 and BRCA2 cancer-predisposing mutations is available on a clinical basis for subjects who are identified to be at high risk for a BRCA1 or BRCA2 cancer-predisposing mutation and for at-risk relatives of an individual with an identified BRCA1 or BRCA2 cancer-predisposing mutation. No currently available technique can guarantee the identification of all cancer-predisposing mutations in the BRCA1 gene or in the BRCA2 gene.

C. Polymorphisms and Their Detection

Variations of the genomic sequence within populations are commonly referred to as polymorphisms. The most common sequence variant consists of base variations at a single base position, and such sequence variants, or polymorphisms, are commonly called single nucleotide polymorphisms ("SNPs"). Many other types of sequence variants are found in the human genome, including microsatellites, insertions, deletions, inversions and copy number variations. Each version of the sequence with respect to the polymorphic site represents a specific allele of the polymorphic site. These sequence variants can all be referred to as polymorphisms, occurring at specific polymorphic sites characteristic of the sequence variant in question. In some instances reference is made to different alleles at a polymorphic site without choosing a reference allele. Alternatively, a reference sequence can be referred to for a particular polymorphic site. The reference allele is sometimes referred to as the "wild-type" allele and it usually is chosen as either the first sequenced allele or as the allele from a "non-affected" individual (e.g., an individual that does not display a trait or disease phenotype). Each individual is either homozygous for one allele of the polymorphism (i.e., both chromosomal copies of the individual have the same nucleotide at the SNP location), or heterozygous (i.e., the two sister chromosomes of the individual contain different nucleotides).

The SNP nomenclature as reported herein refers to the official Reference SNP (rs) ID identification tag as assigned to each unique SNP by the National Center for Biotechnological Information (NCBI), dbSNP database version 125 for the SNPs referred to in Tables 2-8, or dbSNP database version 129 for the SNPs referred to in Tables 10-25, human genome build 35 (in accordance with the UCSC genome browser of the human genome release hg17). Alleles for SNP markers, as referred to herein, refer to the bases A, C, G or T as they occur at the polymorphic site in the SNP assay employed. The person skilled in the art will, however, realize that by assaying or reading the opposite DNA strand, the complementary allele can in each case be measured. Thus, for a polymorphic site (polymorphic marker) characterized by an A/G polymorphism, the assay employed may be designed to specifically detect the presence of one or both of the two bases possible, i.e., A and G. Alternatively, by designing an assay that is designed to detect the opposite strand on the DNA template, the presence of the complementary bases T and C can be measured. Quantitatively (for example, in terms of relative risk), identical results would be obtained from measurement of either DNA strand (+strand or −strand).

Detecting specific polymorphic markers can be accomplished by methods known in the art for detecting sequences at polymorphic sites. For example, standard techniques for genotyping for the presence of SNPs and/or microsatellite markers can be used, such as fluorescence-based techniques (Chen, X. et al., Genome Res 1999; 9(5):492-98), utilizing PCR, LCR, nested PCR and other techniques for nucleic acid amplification. Specific methodologies available for SNP genotyping include, but are not limited to, TaqMan genotyping assays and SNPlex platforms (Applied Biosystems), mass spectrometry (e.g., MassARRAY system from Sequenom), minisequencing methods, real-time PCR, Bio-Plex system (BioRad), CEQ and SNPstream systems (Beckman), Molecular Inversion Probe array technology (e.g., Affymetrix GeneChip), and BeadArray Technologies (e.g., Illumina GoldenGate and Infinium assays). By these or other methods available to the person skilled in the art, one or more alleles at polymorphic markers, including microsatellites, SNPs or other types of polymorphic markers, can be identified.

The person skilled in the art will appreciate that for markers with two alleles present in the population being studied (such as SNPs), and wherein one allele is found in increased frequency in a group of individuals with a trait or disease in the population, compared with controls, the other allele of the marker will be found in decreased frequency in the group of individuals with the trait or disease, compared with controls. In such a case, one allele of the marker (the one found in increased frequency in individuals with the trait or disease) will be the at-risk allele, while the other allele will be a protective allele.

The person skilled in the art will further appreciate that the variants described herein in general do not, by themselves, provide an absolute identification of individuals who will develop breast or ovarian cancer. The variants described herein do, however, indicate increased or decreased likelihood that subjects carrying the at-risk or protective variants of the invention will develop breast or ovarian cancer. This information is extremely valuable in itself, as it can be used, for example, to initiate preventive measures at an early stage, perform exams to monitor the progress and/or appearance of symptoms, or schedule exams at a regular interval to identify early signs of the cancer, so as to be able to apply treatment at an early stage.

D. MicroRNAs and Their Processing

A gene coding for a miRNA may be transcribed, leading to production of a miRNA precursor known as the pri-miRNA. The pri-miRNA may be part of a polycistronic RNA comprising multiple pri-miRNAs. The pri-miRNA may form a hairpin with a stem and loop. The stem may comprise mismatched bases.

The hairpin structure of the pri-miRNA may be recognized by Drosha, which is an RNase III endonuclease. Drosha may recognize terminal loops in the pri-miRNA and cleave approximately two helical turns into the stem to produce a 30-200 nt precursor known as the pre-miRNA. Drosha may cleave the pri-miRNA with a staggered cut typical of Rnase III endonucleases yielding a pre-miRNA stem loop with a 5' phosphate and ~2 nucleotide 3' overhang. Approximately one helical turn of stem (~10 nucleotides) extending beyond the Drosha cleavage site may be essential for efficient processing. The pre-miRNA may then be actively transported from the nucleus to the cytoplasm by Ran-GTP and the export receptor Ex-portion-5.

The pre-miRNA may be recognized by Dicer, which is also an Rnase III endonuclease. Dicer may recognize the double-stranded stem of the pre-miRNA. Dicer may also recognize the 5' phosphate and 3' overhang at the base of the stem loop. Dicer may cleave off the terminal loop two helical turns away from the base of the stem loop leaving an additional 5' phosphate and ~2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. MiRNA* sequences may be found in libraries of cloned miRNAs but typically at lower frequency than the miRNAs.

Although initially present as a double-stranded species with miRNA*, the miRNA may eventually become incorporated as a single-stranded RNA into a ribonucleoprotein complex known as the RNA-induced silencing complex (RISC). Various proteins can form the RISC, which can lead to variability in specificity for miRNA/miRNA* duplexes, binding site of the target gene, activity of miRNA (repress or activate), and which strand of the miRNA/miRNA* duplex is loaded in to the RISC.

When the miRNA strand of the miRNA:miRNA* duplex is loaded into the RISC, the miRNA* may be removed and degraded. The strand of the miRNA:miRNA* duplex that is loaded into the RISC may be the strand whose 5' end is less tightly paired. In cases where both ends of the miRNA:miRNA* have roughly equivalent 5' pairing, both miRNA and miRNA* may have gene silencing activity.

The RISC may identify target nucleic acids based on high levels of complementarity between the miRNA and the mRNA, especially by nucleotides 2-8 of the miRNA. Only one case has been reported in animals where the interaction between the miRNA and its target was along the entire length of the miRNA. This was shown for miR-196 and Hox B8 and it was further shown that miR-196 mediates the cleavage of the Hox B8 mRNA (Yekta et al., Science 2004; 304:594-596). Otherwise, such interactions are known only in plants (Bartel & Bartel, Plant Physiol 2003; 132:709-717).

A number of studies have looked at the base-pairing requirement between miRNA and its mRNA target for achieving efficient inhibition of translation (reviewed by Bartel, Cell 2004; 116:281-297). In mammalian cells, the first 8 nucleotides of the miRNA may be important (Doench & Sharp, GenesDev 2004; 18:504-511). However, other parts of the microRNA may also participate in mRNA binding. Moreover, sufficient base pairing at the 3' can compensate for insufficient pairing at the 5' (Brennecke et al., PloS Biol 2005; 3:e85). Computation studies, analyzing miRNA binding on whole genomes have suggested a specific role for bases 2-7 at the 5' of the miRNA in target binding but the role of the first nucleotide, found usually to be "A" was also recognized (Lewis et al., 2005; Cell 2005; 120:15-20). Similarly, nucleotides 1-7 or 2-8, the "seed", were used Krek et al., Nat Genet 2005; 37:495-500) to identify and validate targets. MiRNAs differ in their basic structure and sequence of nucleotides; however, similarity in seed sequence may suggest similar activity.

The target sites in the mRNA may be in the 5' UTR, the 3' UTR or in the coding region. Interestingly, multiple miRNAs may regulate the same mRNA target by recognizing the same or multiple sites. The presence of multiple miRNA binding sites in most genetically identified targets may indicate that the cooperative action of multiple RISCs provides the most efficient translational inhibition.

miRNAs may direct the RISC to down-regulate gene expression by either of two mechanisms: mRNA cleavage or translational repression. The miRNA may specify cleavage of the mRNA if the mRNA has a certain degree of complementarity to the miRNA. When a miRNA guides cleavage, the cut may be between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity between the miRNA and binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

E. Nucleic Acids and Kits, for Detecting Increased Risk of Cancer

1. Nucleic Acids

Nucleic acids are provided herein. The nucleic acid may comprise the sequence of SEQ ID NOS: 1-199 or variants thereof. The variant may be a complement of the referenced nucleotide sequence. The variant may also be a nucleotide sequence that is substantially identical to the referenced nucleotide sequence or the complement thereof. The variant may also be a nucleotide sequence which hybridizes under stringent conditions to the referenced nucleotide sequence, complements thereof, or nucleotide sequences substantially identical thereto.

The nucleic acid may have a length of from 10 to 250 nucleotides. The nucleic acid may have a length of at least 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 125, 150, 175, 200 or 250 nucleotides. The nucleic acid may be synthesized or expressed in a cell (in vitro or in vivo) using a synthetic gene described herein. The nucleic acid may be synthesized as a single strand molecule and hybridized to a substantially complementary nucleic acid to form a duplex. The nucleic acid may be introduced to a cell, tissue or organ in a single- or double-stranded form or capable of being expressed by a synthetic gene using methods well known to those skilled in the art, including as described in U.S. Pat. No. 6,506,559, which is incorporated by reference.

i. Nucleic Acid Complex

The nucleic acid may further comprise one or more of the following: a peptide, a protein, a RNA-DNA hybrid, an antibody, an antibody fragment, a Fab fragment, and an aptamer. The nucleic acid may also comprise a protamine-antibody fusion protein as described in Song et al., (Nature Biotechnology 2005; 23:709-717) and Rossi (Nature Biotechnology 2005; 23:682-684), the contents of which are incorporated herein by reference. The protamine-fusion protein may comprise the abundant and highly basic cellular protein protamine. The protamine may readily interact with the nucleic acid. The protamine may comprise the entire 51-amino-acid protamine peptide or a fragment thereof. The protamine may be covalently attached to another protein, which may be a Fab. The Fab may bind to a receptor expressed on a cell surface.

ii. Pri-miRNA

The nucleic acid may comprise a sequence of a pri-miRNA or a variant thereof. The pri-miRNA sequence may comprise from 45-30,000, 50-25,000, 100-20,000, 1,000-1,500 or 80-100 nucleotides. The sequence of the pri-miRNA may comprise a pre-miRNA, miRNA and miRNA*, as set forth herein, and variants thereof. The sequence of the pri-miRNA may comprise the sequence of SEQ ID NOS: 22-25 and 132, or variants thereof.

The pri-miRNA may form a hairpin structure. The hairpin may comprise first and second nucleic acid sequence that are substantially complementary. The first and second nucleic acid sequence may be from 37-50 nucleotides. The first and second nucleic acid sequence may be separated by a third sequence of from 8-12 nucleotides. The hairpin structure may have a free energy less than −25 Kcal/mole as calculated by the Vienna algorithm with default parameters, as described in Hofacker et al. (Monatshefte f. Chemie 1994; 125:167-188), the contents of which are incorporated herein. The hairpin may comprise a terminal loop of 4-20, 8-12 or 10 nucleotides. The pri-miRNA may comprise at least 19% adenosine nucleotides, at least 16% cytosine nucleotides, at least 23% thymine nucleotides and at least 19% guanine nucleotides.

iii. Pre-MiRNA

The nucleic acid may also comprise a sequence of a pre-miRNA or a variant thereof. The pre-miRNA sequence may comprise from 45-200, 60-80 or 60-70 nucleotides. The sequence of the pre-miRNA may comprise a miRNA and a miRNA* as set forth herein. The sequence of the pre-miRNA may also be that of a pri-miRNA excluding from 0-160 nucleotides from the 5' and 3' ends of the pri-miRNA. The sequence of the pre-miRNA may comprise the sequence of SEQ ID NOS: 22-25 and 132, or variants thereof.

iv. MiRNA

The nucleic acid may also comprise a sequence of a miRNA (including miRNA*) or a variant thereof. The miRNA sequence may comprise from 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA. The sequence of the miRNA may comprise sequences derived from SEQ ID NOS: 22-25 and 132, or variants thereof. The sequences are in accordance with Sanger Database version 9.2 or 10.

v. Anti-MiRNA

The nucleic acid may also comprise a sequence of an anti-miRNA that is capable of blocking the activity of a miRNA or miRNA*, such as by binding to the pri-miRNA, pre-miRNA, miRNA or miRNA* (e.g., antisense or RNA silencing), or by binding to the target binding site. The anti-miRNA may comprise a total of 5-100 or 10-60 nucleotides. The anti-miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the anti-miRNA may comprise (a) at least 5 nucleotides that are substantially identical or complementary to the 5' of a miRNA and at least 5-12 nucleotides that are substantially complementary to the flanking regions of the target site from the 5' end of the miRNA, or (b) at least 5-12 nucleotides that are substantially identical or complementary to the 3' of a miRNA and at least 5 nucleotide that are substantially complementary to the flanking region of the target site from the 3' end of the miRNA. The sequence of the anti-miRNA may comprise the complement of sequences derived from SEQ ID NOS: 22-25 and 132, or variants thereof.

vi. Binding Site of Target

The nucleic acid may also comprise a sequence of a target miRNA binding site, or a variant thereof. The target site sequence may comprise a total of 5-100 or 10-60 nucleotides. The target site sequence may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62 or 63 nucleotides. The target sequence may comprise at least 5 nucleotides of SEQ ID NOS: 1-21, 90-96 and 98-107, and variants thereof, or of the complementary sequence of SEQ ID NOS: 1-25, 90-96, 98-107 and 132, and variants thereof.

vii. Probes

A probe is also provided comprising a nucleic acid described herein. Probes may be used for screening and diagnostic methods, as outlined below. The probe may be attached or immobilized to a solid substrate, such as a biochip.

The probe may have a length of from 8 to 500, 10 to 100 or 20 to 60 nucleotides. The probe may also have a length of at least 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 220, 240, 260, 280 or 300 nucleotides. The probe may further comprise a linker sequence of from 10-60 nucleotides.

2. Kits

A kit is also provided and may comprise a nucleic acid described herein together with any or all of the following: assay reagents, buffers, probes and/or primers, and sterile saline or another pharmaceutically acceptable emulsion and suspension base. In addition, the kits may include instructional materials containing directions (e.g., protocols) for the practice of the methods described herein.

For example, the kit may be a kit for the amplification, detection, identification or quantification of a target nucleic acid sequence. The kit may comprise a poly(T) primer, a forward primer, a reverse primer, an extension primer and a probe.

Having now generally described the invention, the same will be more readily understood through reference to the following example, which is provided by way of illustration and is not intended to be limiting of the present invention.

EXAMPLES

Example 1

Study Population

The study population was recruited from among Jewish individuals counseled and tested at the Oncogenetics Unit, Sheba Medical Center since Jan. 1, 2000, and from an ongoing study targeting all consecutive breast cancer patients diagnosed and treated at the Sheba Medical Center from 2002 onwards. All participants recruited from the Oncogenetics Unit were high-risk individuals based on well-practiced criteria (Lynch et al., Cancer Genet Cytogenet 1999; 109:91-98), and all study participants were unrelated to each other (i.e., only one patient per family was included). DNA and relevant clinical demographic and pathological data were already available from these individuals and the study was approved by the IRB. Eligible women were genotyped and found to harbor one of the predominant mutations in Jewish Israeli women in either BRCA1 or BRCA2.

The research described herein below in Examples 2-5 encompassed the following subsets of participants, as presented in Table 1:

TABLE 1

Subsets of participants in the study

| | BRCA1 carriers | | BRCA2 carriers | |
|---|---|---|---|---|
| | n | Mean age (y) | n | Mean age (y) |
| Asymptomatic | 160 | 42.0 ± 11.0 | 48 | 42.8 ± 9.7 |
| Breast cancer affected | 140 | 44.4 ± 11.5 | 58 | 45.8 ± 9.1 |
| Ovarian cancer affected | 63 | 51.7 ± 11.4 | 19 | 60.2 ± 10.4 |
| total | 363 | 44.6 ± 11.7 | 125 | 46.86 ± 11.1 |

Of the 363 BRCA1 carriers, 279 were carriers of the 185delAG mutation, three were carriers of the Tyr978X mutation and 81 were carriers of the 5382insC mutation. Ethnic distribution was as follows: Ashkenazi—318; Iraqi—37; Moroccan—1; Syrian—1; Iranian—6. Mean age at diagnosis of breast/ovarian cancer or counseling was 44.6±11.7 years (range 12-91 years).

The BRCA2 carriers had the 6174delT mutation or the 8765delAG mutation, and all were of either Ashkenazi or Yemenite origin. Mean age at diagnosis of breast/ovarian cancer or counseling was 46.86±11.1 years (range 21-74 years).

The differences between the age at diagnosis for breast cancer and age at counseling for asymptomatic cases were not statistically significant.

Example 2

SNP Selection

The following SNPs in sixty-six genes related to the BRCA1/BRCA2 pathway were selected for genotyping using a bioinformatics approach:

SNPs within predicted miR binding sites on transcripts of genes that are known to be expressed in breast cancer tissues/cell lines according to publicly available data or unpublished microarray data from Rosetta Genomics, and on transcripts of critical genes in cancer development. The prediction was based on complementarity between the "seed" of the miRNA and the corresponding sequence on the 3' UTR part of a transcript of a target gene, and in most cases, the SNP was located in the seed-corresponding sequence on the 3' UTR.

SNPs within hairpins (precursors) of miRs known to be expressed in breast cancer.

The forty-two selected SNPs, from the dbSNP database version 125 of NCBI, are presented in Tables 2a and 2b. Their genomic positions are in accordance with the UCSC genome browser of the human genome release hg17 (which corresponds to NCBI human genome build 35).

TABLE 2a

SNPs located in predicted miR binding sites of transcripts of genes related to breast cancer

| Gene | SNP | Chromosome | Observed polymorphism | Binding miR | SEQ ID NO |
|---|---|---|---|---|---|
| CDKN1A | rs10046116 | 6 | A/C | hsa-miR-491 | 149 |
| IGFBP6 | rs1053149 | 12 | A/C | hsa-miR-145 | 150 |
|  |  |  |  | hsa-miR-199a | 151 |
|  | rs6413499 | 12 | A/G | hsa-miR-141 | 152 |
| IGF1R | rs1065305 | 15 | A/T | hsa-miR-449 | 153 |
|  |  |  |  | hsa-miR-34a | 154 |
|  | rs28457673 | 15 | C/G | hsa-miR-16 | 155 |
|  |  |  |  | hsa-miR-497 | 156 |
|  |  |  |  | hsa-miR-15b | 157 |
|  |  |  |  | hsa-miR-107 | 158 |
|  |  |  |  | hsa-miR-103 | 159 |
| ATF1 | rs11169571 | 12 | C/T | hsa-miR-320 | 160 |
|  |  |  |  | hsa-miR-524-5p | 161 |
|  |  |  |  | hsa-miR-9* | 162 |
|  |  |  |  | hsa-miR-516-3p | 163 |
|  |  |  |  | hsa-miR-330-3p | 164 |
|  |  |  |  | hsa-miR-520d-5p | 165 |
| CTSD | rs11555041 | 11 | C/G | hsa-miR-103 | 159 |
|  |  |  |  | hsa-miR-107 | 158 |
|  | rs8839 | 11 | A/C | hsa-miR-193a | 166 |
| IGFBP5 | rs11575213 | 2 | C/T | hsa-miR-92 | 167 |
| MRE11A | rs13447754 | 11 | C/T | hsa-miR-181a | 113 |
|  |  |  |  | hsa-miR-181b | 114 |
|  |  |  |  | hsa-miR-181c | 168 |
|  | rs1805361 | 11 | A/G | hsa-miR-494 | 169 |
|  | rs13447758 | 11 | C/T | hsa-miR-324-5p | 170 |
| PCNA | rs14453 | 20 | A/T | hsa-miR-200c | 171 |
|  |  |  |  | hsa-miR-200b | 172 |
|  | rs3626 | 20 | C/G | hsa-miR-92 | 167 |
| INS | rs3842753 | 11 | A/C | hsa-miR-491 | 149 |
| RB1 (RB) | rs4151631 | 13 | A/T | hsa-miR-92 | 167 |
|  | rs4151634 | 13 | C/T | hsa-miR-494 | 169 |
| PCAF | rs4858770 | 3 | C/T | hsa-miR-30d | 124 |
|  |  |  |  | hsa-miR-30e-5p | 173 |
| POLR2K | rs7924 | 8 | C/G | hsa-miR-106b | 174 |
|  |  |  |  | hsa-miR-106a | 175 |
|  | rs14960 | 8 | A/C | ¹hsa-miR-1 | 176 |
|  | rs11555067 | 8 | C/T | ¹hsa-miR-1 | 176 |
| BAP1 | rs9855479 | 3 | A/G | hsa-miR-125a | 177 |
|  |  |  |  | hsa-miR-125b | 178 |
| ATM | rs227091 | 11 | C/T | hsa-miR-425-3p | 179 |
| KPNA2 | ²rs1059406 | 17 | C/T | hsa-miR-106b | 174 |
|  |  |  |  | hsa-miR-20a | 180 |
|  |  |  |  | hsa-miR-17-5p | 181 |
|  |  |  |  | hsa-miR-93 | 182 |
|  |  |  |  | hsa-miR-106a | 175 |
| BRCA1 | rs4986854 | 17 | C/T | hsa-miR-25 | 119 |
|  |  |  |  | hsa-miR-92 | 167 |
|  |  |  |  | hsa-miR-92b | 183 |
|  |  |  |  | hsa-miR-32 | 184 |
|  | rs1799966 | 17 | A/G | hsa-miR-326 | 185 |
|  | rs4986852 | 17 | A/G | hsa-miR-149 | 130 |
|  | rs4986848 | 17 | C/T | hsa-miR-105 | 186 |
|  | rs799917 | 17 | C/T | hsa-miR-191 | 187 |
|  | rs28897677 | 17 | A/G | hsa-miR-574 | 188 |
|  | rs28897676 | 17 | C/T | hsa-miR-574 | 188 |

TABLE 2a-continued

SNPs located in predicted miR binding sites of transcripts of genes related to breast cancer

| Gene | SNP | Chromosome | Observed polymorphism | Binding miR | SEQ ID NO |
|---|---|---|---|---|---|
| NBN (NBS1) | rs11987887 | 8 | A/C | hsa-miR-186 | 189 |
| TP53 (P53) | rs916132 | 17 | C/T | hsa-miR-29b | 190 |
| | | | | hsa-miR-29a | 191 |
| | | | | hsa-miR-29c | 192 |
| | rs916131 | 17 | A/G | hsa-miR-151 | 193 |

[1]This miR is not known to be expressed in breast cancer; however, the binding site of the miR to the transcript of the gene was validated.
[2]This SNP is outside of the region complementary to the seed but in match with the miR.

TABLE 2b

SNPs located in precursors of miRs expressed in breast cancer

| miR precursor | SNP | Chromosome | Observed polymorphism | miR | SEQ ID NO |
|---|---|---|---|---|---|
| hsa-mir-196a-2 | rs11614913 | 12 | C/T | hsa-miR-196a | 194 |
| hsa-mir-92-1 | rs9589207 | 13 | A/G | hsa-miR-92 | 167 |
| hsa-mir-140 | rs7205289 | 16 | A/C | hsa-miR-140 | 195 |
| hsa-mir-423 | rs6505162 | 17 | A/C | hsa-miR-423 | 196 |
| hsa-mir-125a | rs12975333 | 19 | G/T | hsa-miR-125a | 177 |
| hsa-mir-149 | rs2292832 | 2 | C/T | hsa-miR-149 | 130 |
| hsa-mir-27a | rs11671784 | 19 | A/G | hsa-miR-27a | 110 |
| | rs895819 | 19 | C/T | | |

Example 3

Genotyping using the Sequenom iPLEX™ Assay

SEQUENOM®'s (La-Jolla, Calif.) iPLEX™ assay for SNP genotyping allows performing 24-plex reactions on MassARRAY® System. PCR primers were designed in a region of approximately 100 base pairs around the SNP of interest for the first PCR reaction and an extension primer was designed immediately adjacent to the SNP for the second step of extension PCR during which addition of one base, according to the SNP, occurs.

The assay design was performed in a highly automated fashion by the AssayDesigner Software module. Each pattern of each SNP (homozygous to either allele and heterozygote) was sequenced in 2-3 samples. The starting point of the iPLEX assay was PCR amplification, followed by the addition of shrimp alkaline phosphatase (SAP) to inactivate remaining nucleotides in the reaction. Following brief incubation, the primer extension mixture was added and conducted using a standardized cycling program. Finally, Clean-Resin was added to the mixture to prepare it for deposition on a 384-well SpectroChip®. SpectroChips enable automated readout and data analysis by a Compact™ MALDI-ToF mass spectrometer. Data analysis was performed on the Typer Software Module.

Example 4

Polymorphic Pattern of SNPs

Of the forty-two SNPs genotyped, sixteen exhibited a polymorphic pattern among the study population of BRCA1 and BRCA2 carriers, eleven had a minor allele frequency≥0.05 and nine of them maintained the Hardy-Weinberg Equilibrium. Tables 3a and 3b below provide the SEQ ID NOs of the 16 reference DNA sequences [from the human reference sequence (NCBI Build 35), May 2004] in which a polymorphic pattern of SNPs was found, the location of the SNP within the sequence, the base variants at the SNP and the DNA coding strand of each sequence. Unless stated otherwise, the SNP was located on the same DNA strand coding the sequence. The PCR primers and extension primers used for detecting the SNPs, as described in Example 3 above, are also provided in Tables 3a and 3b.

TABLE 3a

Polymorphic SNPs (in genes related to breast cancer) within predicted miR binding site (BS)

| SNP | Binding miR | SEQ ID NO. of DNA sequence encoding BS | DNA coding strand of miR BS | Location of SNP within sequence, from 5' | SEQ ID NO. of PCR primer Forward | SEQ ID NO. of PCR primer Reverse | Base variant at SNP | SEQ ID NO. of extension primer |
|---|---|---|---|---|---|---|---|---|
| rs11169571 | hsa-miR-320 | 1 | + | 20 | 26 | 42 | C | 58 |
| | hsa-miR-524-5p | 2 | | 16 | | | | |
| | hsa-miR-9* | 3 | | 18 | | | | |
| | hsa-miR-516-3p | 4 | | 18 | | | [1]T | 59 |
| | hsa-miR-330-3p | 5 | | 19 | | | | |
| | hsa-miR-520d-5p | 6 | | 16 | | | | |

TABLE 3a-continued

Polymorphic SNPs (in genes related to breast cancer) within predicted miR binding site (BS)

| SNP | Binding miR | SEQ ID NO. of DNA sequence encoding BS | DNA coding strand of miR BS | Location of SNP within sequence, from 5' | SEQ ID NO. of PCR primer Forward | SEQ ID NO. of PCR primer Reverse | Base variant at SNP | SEQ ID NO. of extension primer |
|---|---|---|---|---|---|---|---|---|
| rs11575213 | hsa-miR-92 | 7 | − | 20 | 27 | 43 | C | 60 |
|  |  |  |  |  |  |  | [1]T | 61 |
| rs3626 | hsa-miR-92 | 8 | − | 16 | 28 | 44 | C | 62 |
|  |  |  |  |  |  |  | [1]G | 63 |
| rs3842753 | hsa-miR-491 | 9 | − | 21 | 29 | 45 | [1]A | 64 |
|  |  |  |  |  |  |  | C | 65 |
| rs4858770 | hsa-miR-30d | 10 | + | 21 | 30 | 46 | [1]C | 66 |
|  | hsa-miR-30e-5p | 11 |  | 19 |  |  | T | 67 |
| rs7924 | hsa-miR-106b | 12 | + | 20 | 31 | 47 | [1]C | 68 |
|  | hsa-miR-106a | 13 |  | 17 |  |  | G | 69 |
| rs8839 | hsa-miR-193a | 14 | − | 18 | 32 | 48 | [1]A | 70 |
|  |  |  |  |  |  |  | C | 71 |
| rs4986854 | hsa-miR-25 | 15 | − | 21 | 33 | 49 | C | 72 |
|  | hsa-miR-92 | 16 |  | 20 |  |  |  |  |
|  | hsa-miR-92b | 17 |  | 20 |  |  | [1]T | 73 |
|  | hsa-miR-32 | 18 |  | 20 |  |  |  |  |
| rs1799966 | hsa-miR-326 | 19 | − | 18 | 34 | 50 | [1]A | 74 |
|  |  |  |  |  |  |  | G | 75 |
| rs4986852 | hsa-miR-149 | 20 | − | 21 | 35 | 51 | A | 76 |
|  |  |  |  |  |  |  | [1]G | 77 |
| rs799917 | hsa-miR-191 | 21 | − | 18 | 36 | 52 | [1]C | 78 |
|  |  |  |  |  |  |  | T | 79 |

TABLE 3b

Polymorphic SNPs in miR precursors of miRs expressed in breast cancer

| SNP | miR precursor comprising SNP | SEQ ID NO. of DNA encoding miR precursor | DNA coding strand of miR precursor | Location of SNP within sequence, from 5' | SEQ ID NO. of PCR primer forward | SEQ ID NO. of PCR primer reverse | Base variant at SNP | SEQ ID NO. of extension primer |
|---|---|---|---|---|---|---|---|---|
| rs11614913 | hsa-mir-196a-2 | 22 | + | 78 | 37 | 53 | [1]C | 80 |
|  |  |  |  |  |  |  | T | 81 |
| rs6505162 | hsa-mir-423 | 23 | + | 87 | 38 | 54 | [1]A | 82 |
|  |  |  |  |  |  |  | C | 83 |
| rs2292832 | hsa-mir-149 | 24 | + | 86 | 39 | 55 | C | 84 |
|  |  |  |  |  |  |  | [1]T | 85 |
| rs11671784 | hsa-mir-27a | [2]25 | − | 36 | 40 | 56 | A | 86 |
|  |  |  |  |  |  |  | [1]G | 87 |
| rs895819 |  |  |  | 40 | 41 | 57 | C | 88 |
|  |  |  |  |  |  |  | [1]T | 89 |

[1]Of the two base variants appearing in the tables (one above the other) for each SNP, the indicated variant is the one presented in the reference sequence in the sequence listing.
[2]The precursor of miR hsa-miR27a is encoded on the negative (−) DNA strand, whereas SNP rs895819 is presented on the positive (+) DNA strand, which is antisense to the miR precursor. In order to match the sequences of the SNP, SEQ ID NO: 25 in the sequence listing is provided as the antisense of the sequence as presented in the cited database.

Example 5

Analysis of Genotyping Results

SNP genotype and allelic distribution were determined by direct counting in the samples. The Arlequin software package was used to detect significant departure from the Hardy-Weinberg Equilibrium (Guo et al. Biometrics 1992; 48:361-372). Kaplan-Meier and Cox regression analyses were performed to compare the different genotypes of each of the sixteen polymorphic SNPs among the tested BRCA1 and BRCA2 carriers, with regard to the risk of breast and ovarian cancer development and the age at diagnosis of cancer. Both assays were done using the SSPS program using the V.15 software. Fisher exact test was used for allele frequency comparisons between group pairs. The Bonferroni corrections and the false discovery rate (FDR) estimations (Benjamini and Hochberg J Roy Statist Soc Ser B 1995: 57: 289-300) were applied to individual test statistics. The following five SNPs showed statistically significant differences: rs3842753 (in SEQ ID NO: 9), rs6505162 (in SEQ ID NO: 23), rs11169571 (in SEQ ID NO: 1), rs3626 (in SEQ ID NO: 8) and rs895819 (in SEQ ID NO: 25).

5.a The rs3842753 SNP (in SEQ ID NO: 9)

The allele distribution at the rs3842753 SNP among the tested BRCA1 and BRCA2 carriers is presented in Table 4 as follows:

TABLE 4

Distribution of rs3842753 genotypes

| | | rs3842753 genotype | | | |
|---|---|---|---|---|---|
| | | AA | AC | CC | Total |
| BRCA1 | asymptomatic | 20 | 64 | 79 | 163 |
| | breast cancer | 10 | 57 | 71 | 138 |
| | ovarian cancer | 3 | 26 | 35 | 64 |
| | Total | 33 | 147 | 185 | 365 |
| BRCA2 | asymptomatic | 3 | 18 | 28 | 49 |
| | breast cancer | 3 | 23 | 32 | 58 |
| | ovarian cancer | 1 | 12 | 6 | 19 |
| | Total | 7 | 53 | 66 | 126 |
| | Total | 40 | 200 | 251 | 491 |

Both Kaplan-Meier and Cox regression analyses showed that homozygosity for the A allele at this SNP affects ovarian cancer risk as well as age at diagnosis of ovarian cancer in BRCA1 carriers. The Cox regression analysis showed that BRCA1 carriers bearing the AC genotype of rs3842753 had a relative risk of 4.782 of developing ovarian cancer when compared with AA homozygotes (p=0.015; 95% Confidence Interval: 1.357-16.857), and CC homozygotes of rs3842753, compared with AA homozygotes, had a relative risk of 3.348 of developing ovarian cancer (p=0.051; 95% Confidence Interval: 0.993-11.296). According to the Kaplan-Meier analysis, the median age at which BRCA1-carrying subjects bearing the AA, AC and CC genotypes at the rs3842753 SNP are diagnosed with ovarian cancer is 80, 56 and 59 years, respectively (p=0.014 AC vs. AA, and p=0.041 CC vs. AA). A Kaplan-Meier plot depicting these results is presented in FIG. 1A.

Accordingly, at the rs3842753 SNP, the C allele was associated with an increased risk for ovarian cancer at a young age, both in the homozygous CC and the heterozygous AC state, as compared with homozygous AA carriers of this SNP, among BRCA1 carriers. The rs3842753 SNP is located in the insulin binding site (SEQ ID NO: 9) of hsa-mir-491 miRNA. Over-expression of insulin receptors, known mediators of a cellular proliferative response, has previously been detected in ovarian cancer cells. Hypothetically, it is possible that carrying two A alleles improves the annealing of the INS mRNA to hsa-mir-491, thus enabling down-regulation of protein translation that leads to lowering the proliferative signal and hence to a decrease in the potential for dysregulated cellular proliferation of ovarian epithelial cells in BRCA1 carriers.

5.b The rs6505162 SNP (in SEQ ID NO: 23)

The allele distribution at the rs6505162 SNP among the tested BRCA1 and BRCA2 carriers is presented in Table 5 as follows:

TABLE 5

Distribution of rs6505162 genotypes

| | | rs6505162 genotype | | | |
|---|---|---|---|---|---|
| | | AA | AC | CC | Total |
| BRCA1 | asymptomatic | 34 | 76 | 46 | 156 |
| | breast cancer | 28 | 59 | 46 | 133 |
| | ovarian cancer | 17 | 21 | 22 | 60 |
| | Total | 79 | 156 | 114 | 349 |

TABLE 5-continued

Distribution of rs6505162 genotypes

| | | rs6505162 genotype | | | |
|---|---|---|---|---|---|
| | | AA | AC | CC | Total |
| BRCA2 | asymptomatic | 15 | 26 | 9 | 50 |
| | breast cancer | 6 | 29 | 22 | 57 |
| | ovarian cancer | 5 | 5 | 9 | 19 |
| | Total | 26 | 60 | 40 | 126 |
| | Total | 105 | 216 | 154 | 475 |

Figure 1B:
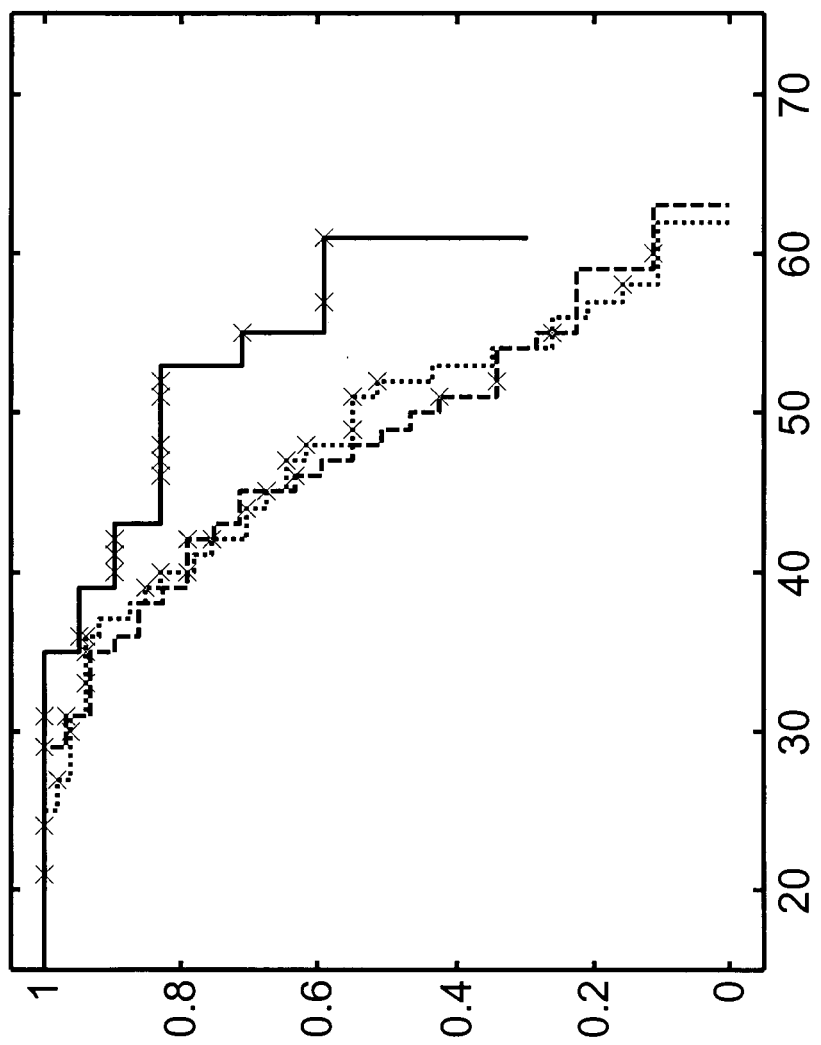

The Cox regression analysis showed that BRCA2 carriers bearing the AC genotype of rs6505162 had a relative risk of 2.837 of developing breast cancer when compared with AA homozygotes (p=0.021; 95% Confidence Interval: 1.174-6.855), and CC homozygotes of rs6505162, compared with AA homozygotes, had a relative risk of 2.772 (p=0.028; 95% Confidence Interval: 1.114-6.9). According to the Kaplan-Meier analysis, the median age at which BRCA2 mutation-carrying subjects bearing the AA, AC and CC genotypes at the rs3842753 SNP are diagnosed with breast cancer is 61, 51 and 49 years, respectively (p=0.017 AC vs. AA, and p=0.016 CC vs. AA). A Kaplan-Meier plot depicting these results is presented in FIG. 1B.

The rs6505162 SNP is located on chromosome 17 within the hsa-mir-423 miRNA precursor (SEQ ID NO: 23), a miRNA whose activity was reportedly increased somatically in breast cancer. In the present study the A allele at this SNP was found to be associated with a decreased risk of developing breast cancer in BRCA2 carriers. The specific gene(s) regulated by this miRNA are not known, and it is therefore difficult to explain its activity or the mechanism by which this SNP affects the age at which breast cancer is diagnosed in BRCA2 mutation carriers.

5.c The rs11169571 SNP (in SEQ ID NO: 1)

The allele distribution at the rs11169571 SNP among the tested BRCA1 and BRCA2 carriers is presented in Table 6 as follows:

TABLE 6

Distribution of rs11169571 genotypes

| | | rs11169571 genotype | | | |
|---|---|---|---|---|---|
| | | CC | CT | TT | Total |
| BRCA1 | asymptomatic | 12 | 60 | 78 | 150 |
| | breast cancer | 12 | 58 | 66 | 136 |
| | ovarian cancer | 11 | 19 | 32 | 62 |
| | Total | 35 | 137 | 176 | 348 |
| BRCA2 | asymptomatic | 4 | 22 | 23 | 49 |
| | breast cancer | 4 | 26 | 25 | 55 |
| | ovarian cancer | 1 | 6 | 12 | 19 |
| | Total | 9 | 54 | 60 | 123 |
| | Total | 44 | 191 | 236 | 471 |

The Cox regression analysis revealed that BRCA2 carriers bearing the CT heterozygote genotype of rs11169571 had a relative risk of 2.049 of developing breast or ovarian cancer when compared with homozygotes for the frequent T allele (p=0.005; 95% Confidence Interval: 1.236-3.395). CC homozygotes also had a higher risk for developing breast or ovarian cancer than homozygous wild-type TT carriers.

Figure 1C:
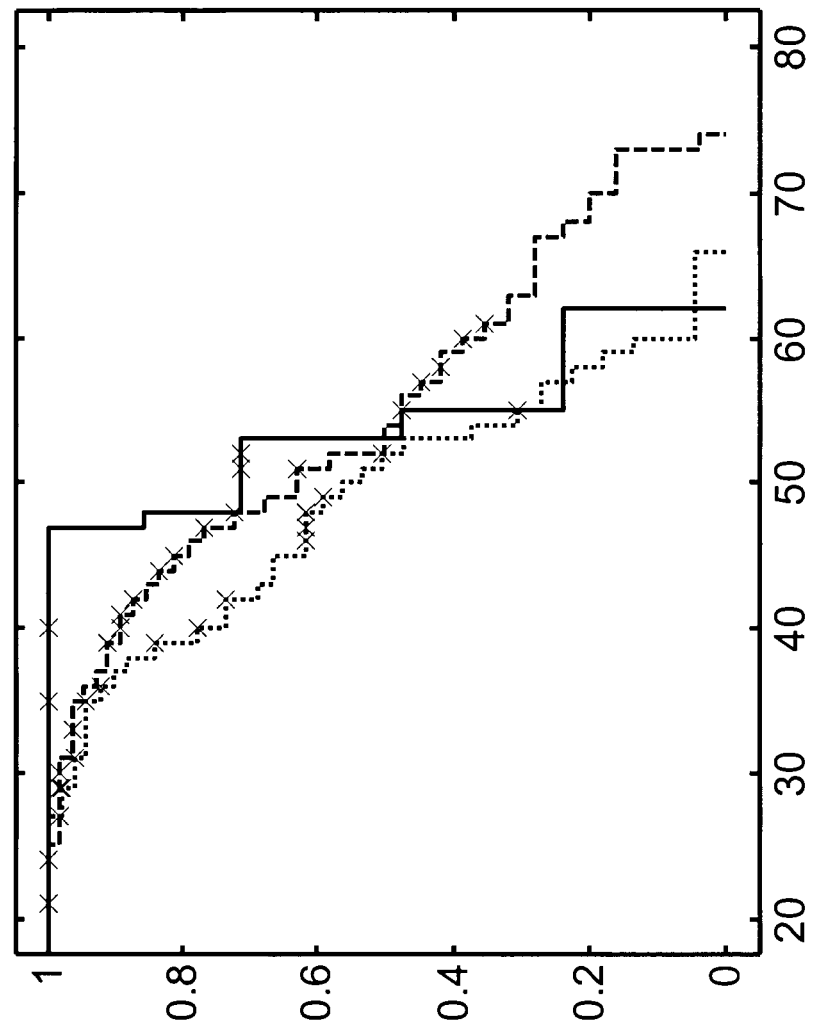

According to the Kaplan-Meier analysis, the median age at which BRCA2-carrying subjects bearing the CC, CT and TT genotypes at the rs11169571 SNP are diagnosed with breast or ovarian cancer is 53, 49 and 56 years, respectively (p=0.005 CT vs. TT). A Kaplan-Meier plot depicting these results is presented in FIG. 1C.

Accordingly, at the rs11169571 SNP, the heterozygous CT genotype was associated with an increased risk of developing breast or ovarian cancer, among BRCA2 carriers. The rs11169571 SNP is located in the ATF1 gene binding site seed of miR-320 (SEQ ID NO: 1). The ATF1 gene is located in 12q13 and encodes a 271-amino acid nuclear protein. ATF1 is a DNA binding protein and cAMP-inducible transcription factor [cAMP-responsive enhancer-binding protein (CRE), like CREB]. The protein possesses a basic motif and a leucine homodimer and ATF-1/CREB heterodimers. miR-320 co-localizes to genomic areas displaying DNA copy loss in ovarian cancer, breast cancer and malignant melanoma (Zhang et al., Proc Natl Acad Sci USA. 2006; 103(24):9136-9141). Blenkiron et al. (Genome Biol 2007; 8(10):R214) found a connection between breast cancer and low levels of miR-320 expression. In that study the researchers identified 133 miR-NAs expressed in human breast and breast tumors. Strong associations between miR-33 and miR-320 expression and genomic alterations was found, suggesting that chromosomal change is a possible mechanism for mis-expression of these genes in primary human breast cancers.

Figure 2:
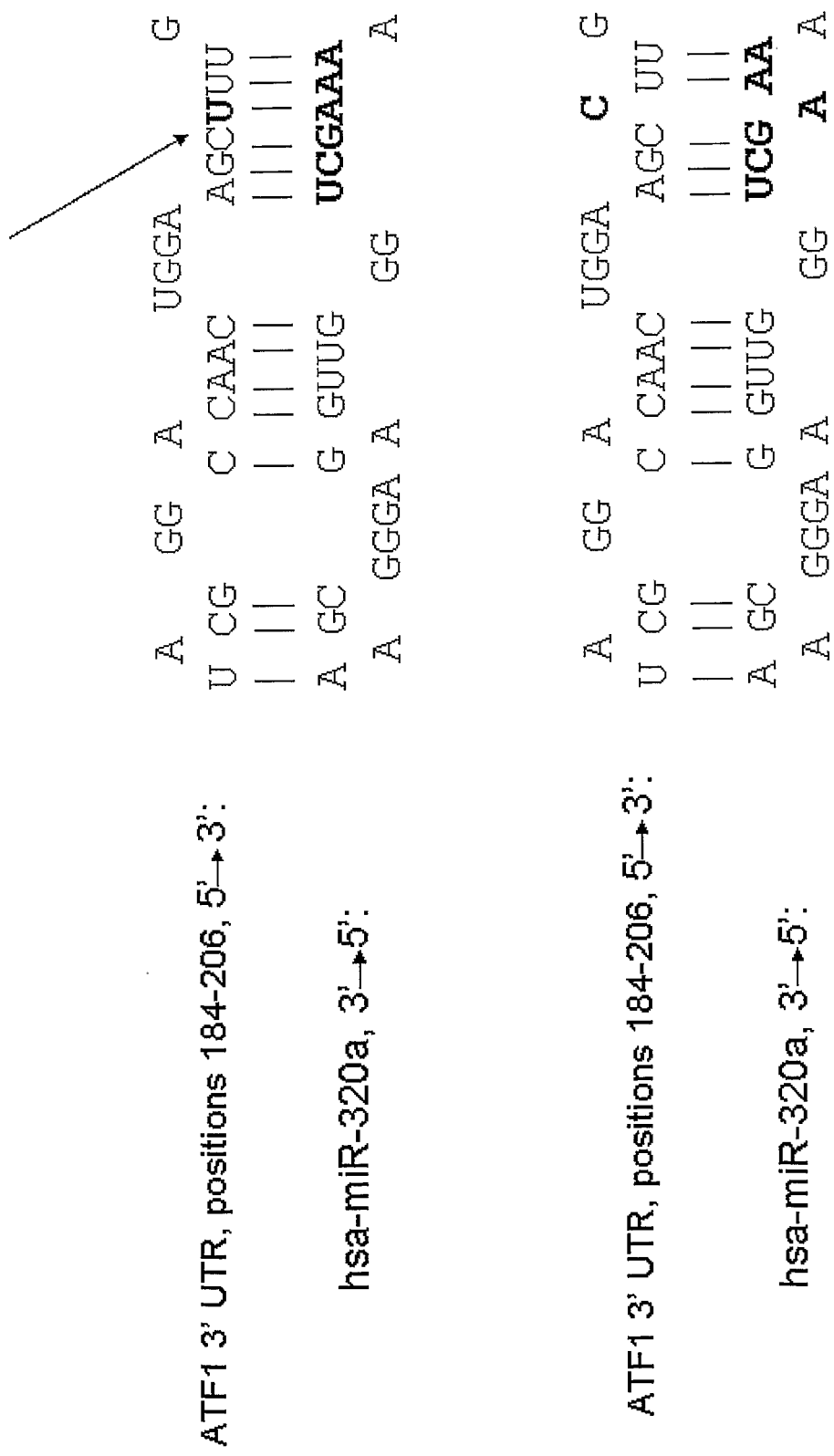
FIG. 2 shows hsa-miR-320a (SEQ ID NO: 160) and its predicted binding site over the ATF1 3' UTR, shown one below the other. The bases which are involved in base pairing are shown with a vertical line between them. The rest of the bases are shown in the upper and lower rows, for the 3' UTR and the miRNA, respectively. hsa-miR-320a is a representative of the miR-320a-d miRNA family, whose members all share a common seed region: AAAGCU (in bold). SNP rs11169571 is indicated by the arrow. When the SNP variant is 'U' (corresponding to T in the DNA), then the miRNA seed is in perfect match with the 3' UTR. Otherwise, there is a mismatch between the seed region and its complementary sequence.

The exact mechanistic-biological effect of the rs11169571 SNP on miRNA binding or effect on gene regulation is not known. However, since SNP rs11169571 is located on a binding site seed of miR-320 (SEQ ID NO: 1), it is possible that the SNP over the ATF1 binding site interferes with the annealing of miR-320 to ATF1 mRNA, thus affecting regulation of the gene and promoting uncontrolled cellular proliferation. According to this scenario, the 'T' allele is part of a functional miRNA binding site, while the 'C' allele causes non-functionality of the miRNA binding site (FIG. 2).

5.d The rs3626 SNP (in SEQ ID NO: 8)

The allele distribution at the rs3626 SNP among the tested BRCA1 and BRCA2 carriers is presented in Table 7 as follows:

TABLE 7

Distribution of rs3626 genotypes

| | | rs3626 genotype | | | |
|---|---|---|---|---|---|
| | | GG | CG | CC | Total |
| BRCA1 + BRCA2 | asymptomatic | 8 | 43 | 147 | 198 |
| | breast cancer | 3 | 40 | 141 | 185 |
| | ovarian cancer | 3 | 18 | 33 | 54 |
| | Total | 14 | 101 | 321 | 436 |

Figure 1D:
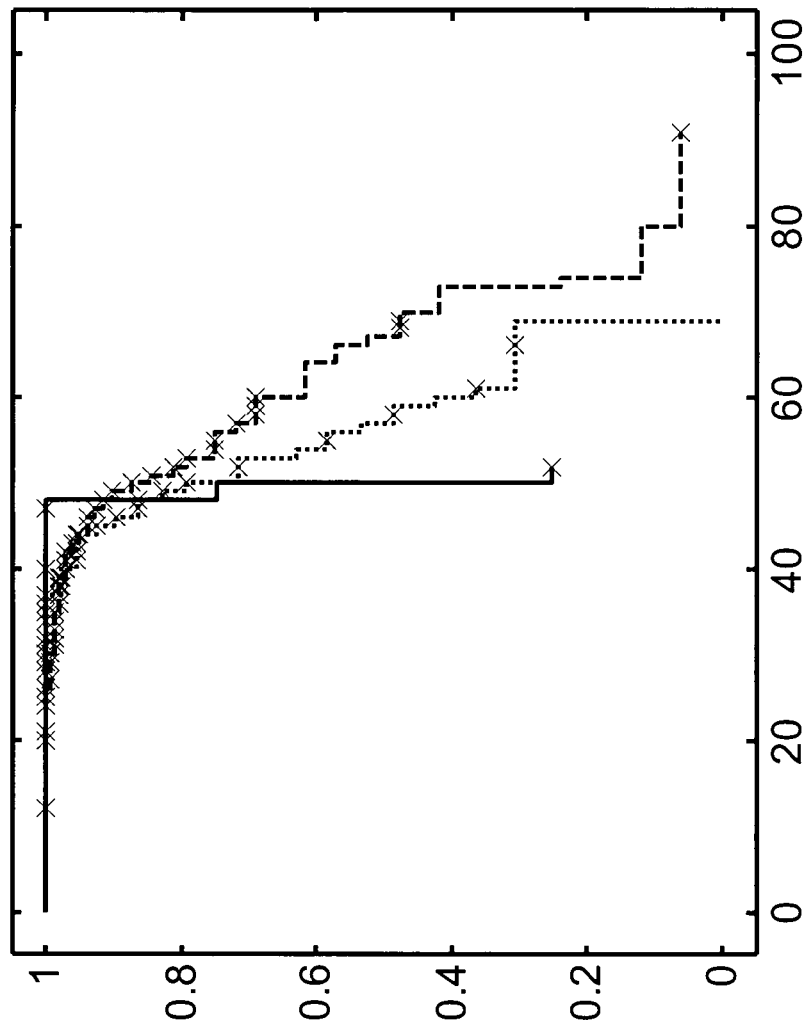

The Cox regression analysis showed that among the combined group of BRCA1 and BRCA2 carriers, subjects bearing the CG genotype of rs3626 had a relative risk of 2.098 of developing ovarian cancer when compared with GG homozygotes (p=0.012; 95% Confidence Interval: 1.175-3.745). According to the Kaplan-Meier analysis, the median age at which the combined group of BRCA1- and BRCA2-carrying subjects bearing the GG, CG and CC genotypes at the rs3626 SNP are diagnosed with ovarian cancer is 67, 57 and 50 years, respectively (p=0.014 CG vs. GG). A Kaplan-Meier plot depicting these results is presented in FIG. 1D. Accordingly, at the rs3626 SNP, the homozygous CC genotype was associated with an increased risk of developing ovarian cancer among BRCA1/2 carriers.

SNP rs3626 is located on chromosome 20 within the gene PCNA binding site to hsa-miR-92 (SEQ ID NO: 8). The pre-miRNA gene is located within a chromosomal area (on chromosome 13) that is frequently deleted in breast cancer. PCNA (proliferating cell nuclear antigen), which encodes a protein that enables DNA polymerase delta to bind to DNA, is over-expressed in breast and ovarian cancer, and may serve as a biomarker for distinguishing between normal and cancerous tissues (Malkas L H et al., Proc Natl Acad Sci USA 2006; 103:19472-19477). These observations suggest that down-regulation of PCNA might affect the risk of developing ovarian cancer. In the present study, BRCA1 and BRCA2 carriers which are CG heterozygous for SNP rs3626 have a significantly higher risk of developing ovarian cancer, compared with carriers of the homozygous GG genotype of this SNP. This increased risk may result from decreased binding of hsa-miR-92 to the PCNA mRNA, leading to gene deregulation, with an increase in protein levels resulting in uncontrolled ovarian epithelial cellular proliferation.

5.e The rs895819 SNP (in SEQ ID NO: 25)

The allele distribution at the rs895819 SNP among the tested BRCA1 and BRCA2 mutation carriers is presented in Table 8 as follows:

TABLE 8

Distribution of rs895819 genotypes

| | | rs895819 genotype | | | |
|---|---|---|---|---|---|
| | | CC | CT | TT | Total |
| BRCA1 | asymptomatic | 13 | 61 | 75 | 149 |
| | breast cancer | 9 | 62 | 61 | 132 |
| | ovarian cancer | 1 | 27 | 35 | 63 |
| | Total | 23 | 150 | 171 | 344 |
| BRCA2 | asymptomatic | 2 | 21 | 26 | 49 |
| | breast cancer | 2 | 16 | 37 | 55 |
| | ovarian cancer | 2 | 7 | 8 | 17 |
| | Total | 6 | 44 | 71 | 121 |
| | Total | 29 | 194 | 242 | 465 |

As is evident from the data presented in Table 8, the common allele in the study population (=primarily Ashkenazi Jews) is the T allele, a finding that is not reported for non-Jewish populations, in which the C allele is more frequently detected.

Figure 1E:
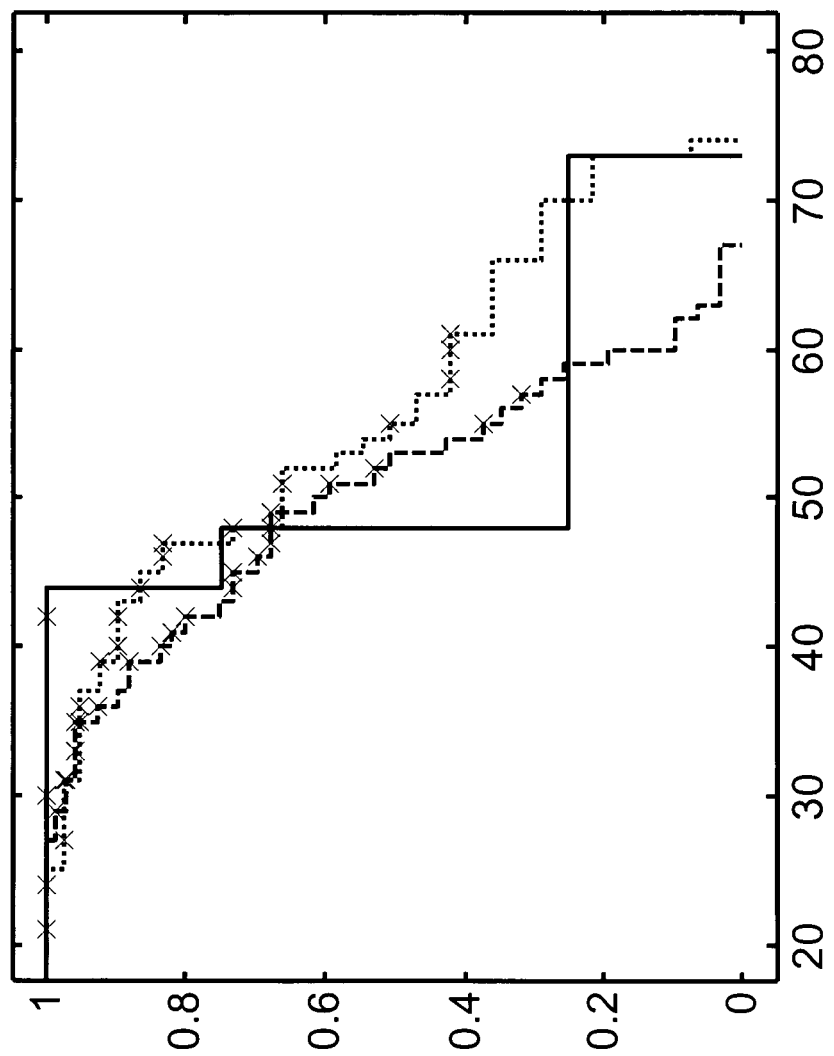

The Cox regression analysis showed that BRCA2 carriers bearing the heterozygous genotype CT of rs895819 have a significantly lower risk of developing breast or ovarian cancer than subjects who are TT homozygotes at this SNP (relative risk 0.512, p=0.013; 95% Confidence of Interval: 0.302-0.866). CC homozygotes had lower risk of developing breast or ovarian cancer than TT homozygotes. According to the Kaplan-Meier analysis, the median age at which BRCA2-carrying subjects bearing the CC, CT and TT genotypes at the rs895819 SNP are diagnosed with breast or ovarian cancer is 53, 57 and 50 years, respectively (p=0.007 for CT vs. TT). A Kaplan-Meier plot depicting these results is presented in FIG. 1E.

The rs895819 SNP is located in the hsa-miR-27a precursor (SEQ ID NO: 25). hsa-miR-27a localizes to chromosome 19, and is reportedly down-regulated in breast, colon, lung, pancreas, prostate and stomach cancer (Volinia et al., Proc Natl Acad Sci USA 2006; 103(7):2257-2261), and up-regulated in head and neck cancer cell lines (Tran et al. Biochem Biophys Res Commun 2007; 358:12-17).

miR-27a was found to be involved, along with miR-451, in activating MDR1 (multidrug resistance gene) expression that endows cancer cells with resistance to various chemotherapy treatments. These miRs are up-regulated in ovarian and cervix cancer cell lines that are resistant to chemotherapy (Zhu H, Wu H, Liu X et al., (2008) Biochem Pharmacol (Epub ahead of print)). In another study, miR-27a reportedly inhibited ZBTB10 expression, which, in turn, inhibited the expression of angiogenesis-related proteins Sp1, Sp3 and Sp4. Treatment of breast cancer cells with miR-27a antisense led to ZBTB10 increase and Sp1, Sp3 and Sp4 decrease and concomitantly to a decrease in cellular survival and levels of angiogenesis proteins VEGF, VEGFR1 and survivin (Mertens-Talcott S U et al., Cancer Res 2007; 67:11001-11011).

Example 6

Polymorphic Pattern of SNPs

An additional group of sixty SNPs was chosen from dbSNP database version 129 for genotyping in BRCA1/2 mutation carriers. The SNPs were divided into three groups:
miR-related SNPs associated with breast cancer and appearing in the literature
SNP on miR precursors expressed in breast cancer in microarray data (median signal>1000 in at least one in five different breast cancer histological types; twenty samples in total)
SNPs on validated and predicted miR targets expressed in breast cancer. The miR targets were taken from Miranda August 2008 and Tarbase 4.2 versions.

Fourteen SNPs were found to be significant and were genotyped in a study population of 630 patients, depicted in Table 9 below.

TABLE 9

Subsets of participants in the study

|  | BRCA1 carriers n | BRCA2 carriers n |
| --- | --- | --- |
| Asymptomatic | 197 | 70 |
| Breast cancer affected | 175 | 86 |
| Ovarian cancer affected | 79 | 23 |
| total | 451 | 179 |

All fourteen SNPs were shown to exhibit a polymorphic pattern among the study population of BRCA1 and BRCA2 carriers. Tables 10a and 10b below provide the SEQ ID NOs of the fourteen DNA sequences encoding miR binding sites in which a polymorphic pattern of SNPs was found, the base variants at the SNP, the binding miRs, together with their SEQ ID NOs and the location of the SNP within the sequence. The same fourteen SNPS are shown in Table 11, which provides further information on the tissue in which each SNP was identified, together with identification of the BRCA gene and a p-value indicating the statistical significance of the correlation between the SNP and the BRCA gene.

TABLE 10a

Polymorphic SNPs (in genes related to breast cancer) with predicted miR binding site (BS)

| Target Gene | SNP | Observed polymorphism | SEQ ID NO of sequence encoding BS | Binding miR | miR SEQ ID NO | Location of SNP within sequence from 5' |
| --- | --- | --- | --- | --- | --- | --- |
| BNIP3L | rs1042992[1] | C/T | 90 | hsa-miR-23a | 108 | 3 |
|  |  |  |  | hsa-miR-23b | 109 | 3 |
| NRIP1 | rs1056930[1] | A/G | 91 | hsa-miR-27a | 110 | 5 |
|  |  |  |  | hsa-miR-27b | 111 | 5 |
| PALLD | rs1071738[1] | C/G | 92 | hsa-miR-23a | 108 | 3 |
|  |  |  |  | hsa-miR-23b | 109 | 3 |
|  |  |  | 93 | hsa-miR-182 | 112 | 19 |
|  |  |  | 94 | hsa-miR-181a | 113 | 5 |
|  |  |  |  | hsa-miR-181b | 114 | 5 |
| MET | rs1621[1] | A/G | 95 | hsa-miR-199a-3p | 115 | 18 |
|  |  |  | 96 | hsa-miR-101 | 116 | 14 |
|  |  |  |  | hsa-miR-144 | 117 | 14 |
| TACC2 | rs3763763[1] | A/C | 98 | hsa-miR-25 | 119 | 15 |
|  |  |  | 98 | hsa-miR-92a | 120 | 15 |
| CSK | rs7085[1] | C/T | 99 | hsa-miR-140-5p | 121 | 10 |
|  |  |  | 100 | hsa-miR-299-5p | 122 | 11 |
| TGFBR1 | rs868[1] | A/G | 101 | let-7 family | 97, 133-148 | 10 |
| IRS2 | rs2289047[2] | A/G/T | 102 | hsa-miR-30a | 123 | 7 |
|  |  |  |  | hsa-miR-30d | 124 | 7 |
| ESR1 | rs2747648[2,3] | (C/T) | 103 | hsa-miR-1298 (Miranda) | 125 | 13 |
| IGF1R | rs28674628[2] | (A/G) | 104 | hsa-miR-151-5p | 127 | 6 |
| ATR | rs35664313[2] | (—/G) | 105 | hsa-miR-34a | 128 | 16-17 |
| BRCA1 | rs8176318[2] | (G/T) | 106 | hsa-miR-345 | 129 | 9 |
|  |  |  | 107 | hsa-miR-149 | 130 | 10 |

[1]The PicTar and TargetScan algorithms were used to predict the miR binding sites. The connection between these SNPs and miRNA binding sites was first identified in Chen K and Rajewsky N. Nature Genetics 2006; 38(12): 1452-1456.
[2]The Miranda algorithm was used to predict the miR binding site.
[3]This SNP was first associated with breast cancer in BRCA1/2 mutation-negative patients by Tchatchou et al. Carcinogenesis 2008; 30(1): 59-64.

TABLE 10b

Polymorphic SNPs in miR precursors of miRs expressed in breast cancer

| SNP | Observed polymorphism | miR precursor comprising SNP | SEQ ID NO | Mature miRNA | SEQ ID NO | Location of SNP within sequence, from 5' |
|---|---|---|---|---|---|---|
| rs895819 | C/T | hsa-mir-27a[1] | 25 | hsa-miR-27a<br>hsa-miR-27a* | 110<br>197 | 40 |
| rs2910164 | C/G | hsa-mir-146a | 132 | hsa-miR-146a<br>hsa-miR-146a* | 198<br>199 | 60 |

[1]The precursor of miR hsa-miR27a is encoded on the negative (−) DNA strand, whereas SNP rs895819 is presented on the positive (+) DNA strand, which is antisense to the miR precursor and exhibits C/T polymorphism (the minus strand exhibits G/A polymorphism). In order to match the sequences of the SNP, SEQ ID NO: 25 in the sequence listing is provided as the antisense of the sequence as presented in the cited database.

TABLE 11

Polymorphic SNPs

| SNP | Observed Polymorphism | Tissue | BRCA gene | p-value |
|---|---|---|---|---|
| rs1042992 | C/T | Ovary | BRCA1 + 2 | 0.011 |
| rs1042992 | C/T | Ovary | BRCA1 | 0.033 |
| rs1042992 | C/T | Ovary + Breast | BRCA1 + 2 | 0.045 |
| rs1056930 | A/G | Ovary | BRCA2 | 0.037 |
| rs1056930 | A/G | Ovary | BRCA1 + 2 | 0.017 |
| rs1056930 | A/G | Ovary | BRCA1 | 0.034 |
| rs1056930 | A/G | Ovary | BRCA1 | 0.017 |
| rs1071738 | C/G | Ovary + Breast | BRCA1 + 2 | 0.033 |
| rs1071738 | C/G | Ovary + Breast | BRCA1 | 0.023 |
| rs1071738 | C/G | Ovary + Breast | BRCA1 | 0.039 |
| rs1071738 | C/G | Ovary | BRCA1 | 0.028 |
| rs1071738 | C/G | Ovary + Breast | BRCA1 | 0.0066 |
| rs1071738 | C/G | Ovary + Breast | BRCA1 | 0.027 |
| rs1621 | A/G | Breast | BRCA2 | 0.0079 |
| rs2289047 | A/G/T | Ovary + Breast | BRCA1 + 2 | 0.034 |
| rs2747648 | C/T | Ovary | BRCA1 | 0.035 |
| rs2747648 | C/T | Breast | BRCA2 | 6.60E−05 |
| rs2747648 | C/T | Ovary | BRCA1 | 0.035 |
| rs2747648 | C/T | Breast | BRCA2 | 6.60E−05 |
| rs2747648 | C/T | Breast | BRCA2 | 0.0038 |
| rs2747648 | C/T | Breast | BRCA2 | 0.0038 |
| rs28674628 | A/G | Breast | BRCA1 + 2 | 0.043 |
| rs28674628 | A/G | Breast | BRCA1 | 0.00093 |
| rs28674628 | A/G | Ovary + Breast | BRCA1 | 0.021 |
| rs28674628 | A/G | Breast | BRCA1 | 0.00082 |
| rs28674628 | A/G | Ovary + Breast | BRCA1 | 0.031 |
| rs2910164 | C/G | Ovary + Breast | BRCA1 | 0.037 |
| rs2910164 | C/G | Breast | BRCA2 | 0.034 |
| rs2910164 | C/G | Ovary + Breast | BRCA2 | 0.047 |
| rs35664313 | —/G | Ovary | BRCA1 + 2 | 0.024 |
| rs35664313 | —/G | Ovary | BRCA2 | 0.039 |
| rs35664313 | —/G | Ovary + Breast | BRCA1 | 0.033 |
| rs35664313 | —/G | Ovary | BRCA1 + 2 | 0.017 |
| rs35664313 | —/G | Ovary | BRCA1 | 0.045 |
| rs35664313 | —/G | Breast | BRCA2 | 0.039 |
| rs35664313 | —/G | Ovary | BRCA1 + 2 | 0.035 |
| rs35664313 | —/G | Ovary | BRCA2 | 0.04 |
| rs3763763 | A/C | Ovary | BRCA2 | 0.048 |
| rs7085 | C/T | Ovary + Breast | BRCA1 | 0.044 |
| rs7085 | C/T | Ovary | BRCA1 | 0.013 |
| rs7085) | C/T | Ovary + Breast | BRCA1 | 0.0099 |
| rs8176318 | G/T | Ovary | BRCA1 + 2 | 0.023 |
| rs868 | A/G | Ovary | BRCA1 | 0.042 |
| rs895819 | C/T | Ovary | BRCA2 | 0.03 |
| rs895819 | C/T | Ovary + Breast | BRCA2 | 0.018 |
| rs895819 | C/T | Ovary | BRCA2 | 0.013 |
| rs895819 | C/T | Ovary + Breast | BRCA2 | 0.031 |
| rs895819 | C/T | Ovary | BRCA2 | 0.0092 |

Example 7

Analysis of Genotyping Results

Kaplan-Meier analysis was performed to compare the different genotypes of each of the fourteen polymorphic SNPs among the tested BRCA1 and BRCA2 carriers, with regard to the risk of breast and ovarian cancer development and the age at diagnosis of cancer.

7.a The rs1071738 SNP (in SEQ ID NOS: 92-94)

The allele distribution at the rs1071738 SNP among the tested BRCA1 and BRCA2 carriers is presented in Table 12 as follows:

TABLE 12

Distribution of rs1071738 genotypes

| | | rs1071738 genotype | | | |
|---|---|---|---|---|---|
| | | GG | GC | CC | Total |
| BRCA1 | asymptomatic | 57 | 94 | 20 | 171 |
| | breast cancer | 59 | 85 | 17 | 161 |
| | ovarian cancer | 25 | 36 | 13 | 74 |
| | Total | 141 | 215 | 50 | 406 |
| BRCA2 | asymptomatic | 12 | 30 | 8 | 50 |
| | breast cancer | 26 | 37 | 10 | 73 |
| | ovarian cancer | 10 | 10 | 1 | 21 |
| | Total | 48 | 77 | 19 | 144 |
| | Total | 189 | 292 | 69 | 550 |

Figure 3A:
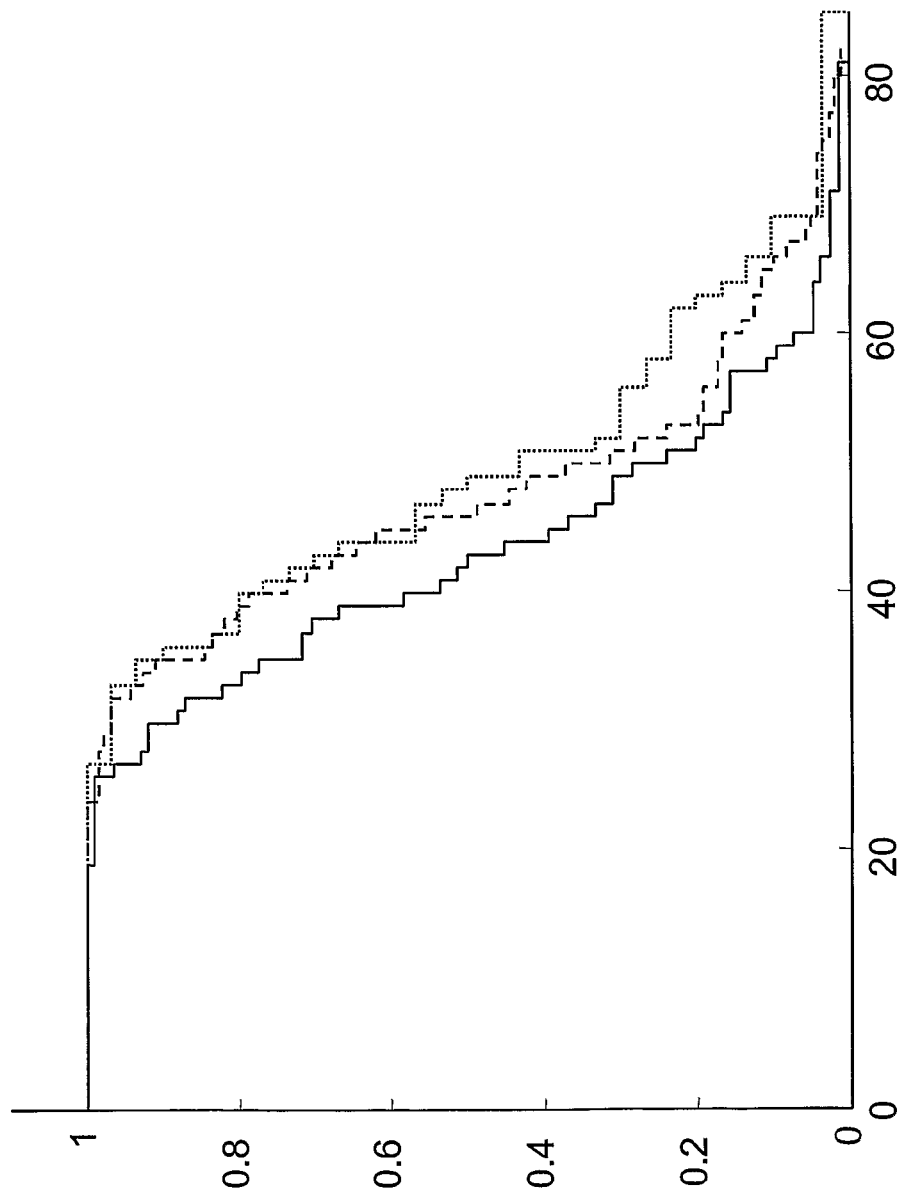
FIGS. 3A-3I are Kaplan-Meier plots depicting the age-dependent development of breast or ovarian cancer in BRCA1 and/or BRCA2 carriers. The y-axis represents the fraction of subjects who developed cancer and the x-axis represents the age of the subjects (in years). Each drop in the curve represents a subject diagnosed with breast or ovarian cancer.

According to the Kaplan-Meier analysis, the median age at which BRCA1-carrying subjects bearing the GG, GC and CC genotypes at the rs1071738 SNP are diagnosed with both breast and ovarian cancer is 42, 46 and 49 years, respectively (p=0.027 GG vs. CC). A Kaplan-Meier plot depicting these results is presented in FIG. 3A. Accordingly, at the rs1071738 SNP, the homozygous CC genotype was associated with a decreased risk of developing breast or ovarian cancer among BRCA1 carriers.

7.b The rs2747648 SNP (in SEQ ID NO: 103)

The allele distribution at the rs2747648 SNP among the tested BRCA1 and BRCA2 carriers is presented in Table 13 as follows:

TABLE 13

Distribution of rs2747648 genotypes

|  |  | rs2747648 genotype | | | |
|---|---|---|---|---|---|
|  |  | TT | CT | CC | Total |
| BRCA1 | asymptomatic | 146 | 20 | 0 | 166 |
|  | breast cancer | 146 | 11 | 2 | 159 |
|  | ovarian cancer | 63 | 9 | 0 | 72 |
|  | Total | 355 | 40 | 2 | 397 |
| BRCA2 | asymptomatic | 53 | 3 | 0 | 56 |
|  | breast cancer | 65 | 10 | 0 | 75 |
|  | ovarian cancer | 18 | 3 | 0 | 21 |
|  | Total | 136 | 16 | 0 | 152 |
|  | Total | 491 | 56 | 2 | 549 |

Figure 3B:
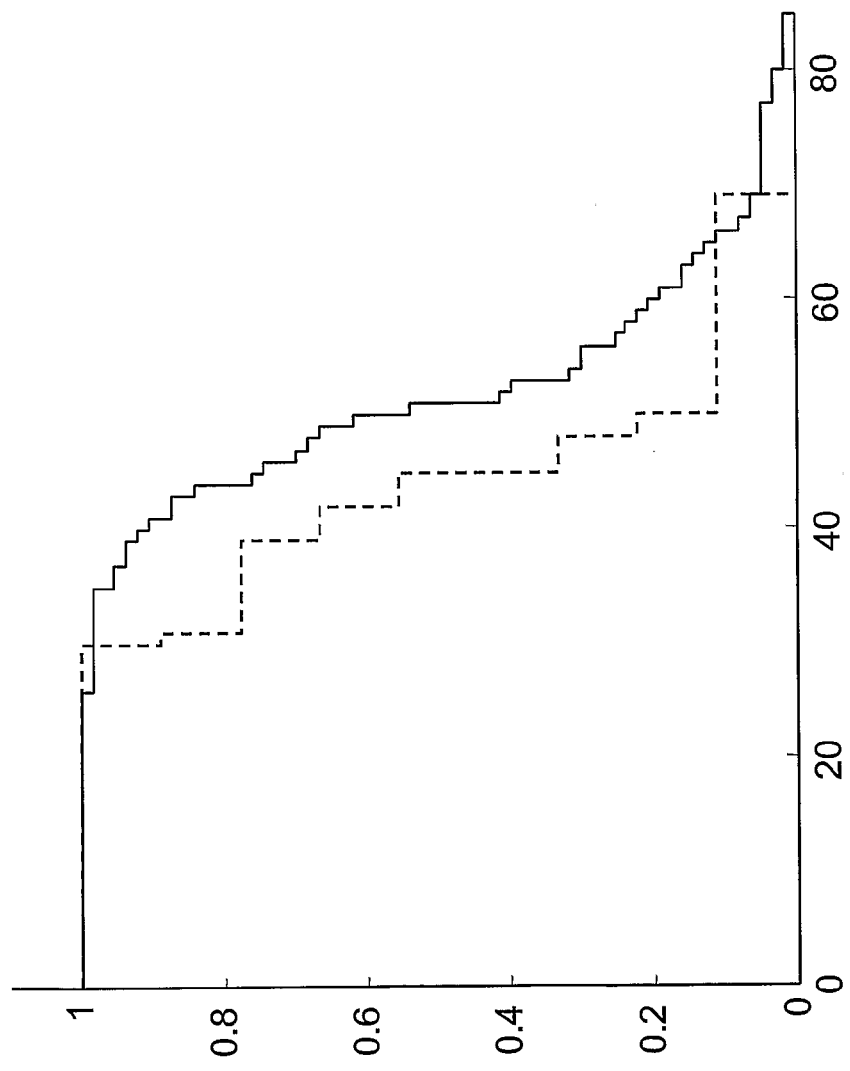

According to the Kaplan-Meier analysis, the median age at which BRCA1-carrying subjects bearing the TT and CT genotypes at the rs2747648 SNP are diagnosed with ovarian cancer is 51 and 45, respectively. A Kaplan-Meier plot depicting these results is presented in FIG. 3B. Accordingly, at the rs2747648 SNP, the homozygous TT genotype was associated with a decreased risk of developing ovarian cancer among BRCA1 carriers.

Figure 3C:
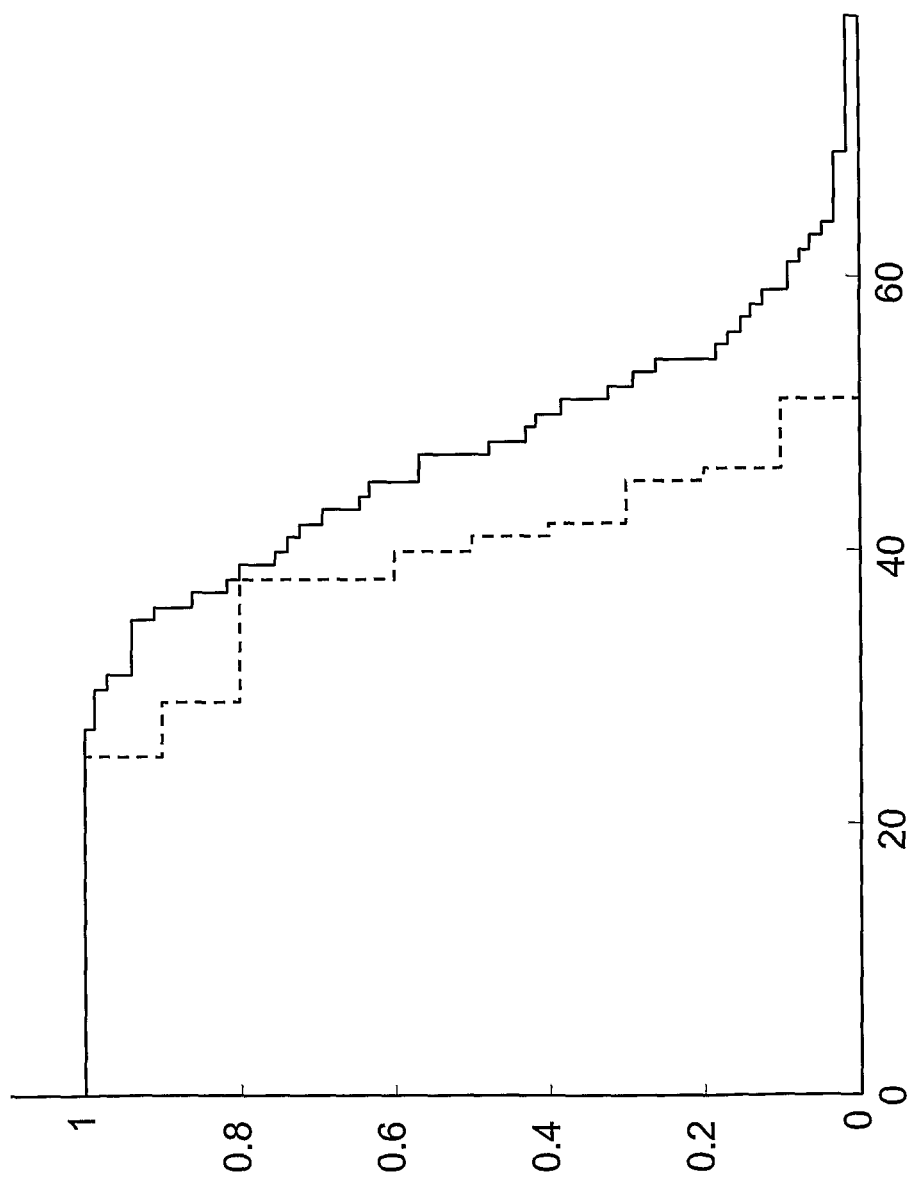

According to the Kaplan-Meier analysis, the median age at which BRCA2-carrying subjects bearing the TT and CT genotypes at the rs2747648 SNP are diagnosed with breast cancer is 47 and 40 years, respectively (p=0.004 TT vs. CT). A Kaplan-Meier plot depicting these results is presented in FIG. 3C. Accordingly, at the rs2747648 SNP, the homozygous TT genotype was associated with a decreased risk of developing breast cancer among BRCA2 carriers.

7.c The rs28674628 SNP (in SEQ ID NO: 104)

The allele distribution at the rs28674628 SNP among the tested BRCA1 and BRCA2 carriers is presented in Table 14 as follows:

TABLE 14

Distribution of rs28674628 genotypes

|  |  | rs28674628 genotype | | | |
|---|---|---|---|---|---|
|  |  | AA | GA | GG | Total |
| BRCA1 | asymptomatic | 180 | 7 | 1 | 188 |
|  | breast cancer | 157 | 9 | 1 | 167 |
|  | ovarian cancer | 74 | 3 | 0 | 77 |
|  | Total | 411 | 19 | 2 | 432 |
| BRCA2 | asymptomatic | 63 | 0 | 0 | 63 |
|  | breast cancer | 77 | 5 | 0 | 82 |
|  | ovarian cancer | 18 | 0 | 0 | 18 |
|  | Total | 158 | 5 | 0 | 163 |
|  | Total | 569 | 24 | 2 | 595 |

Figure 3D:
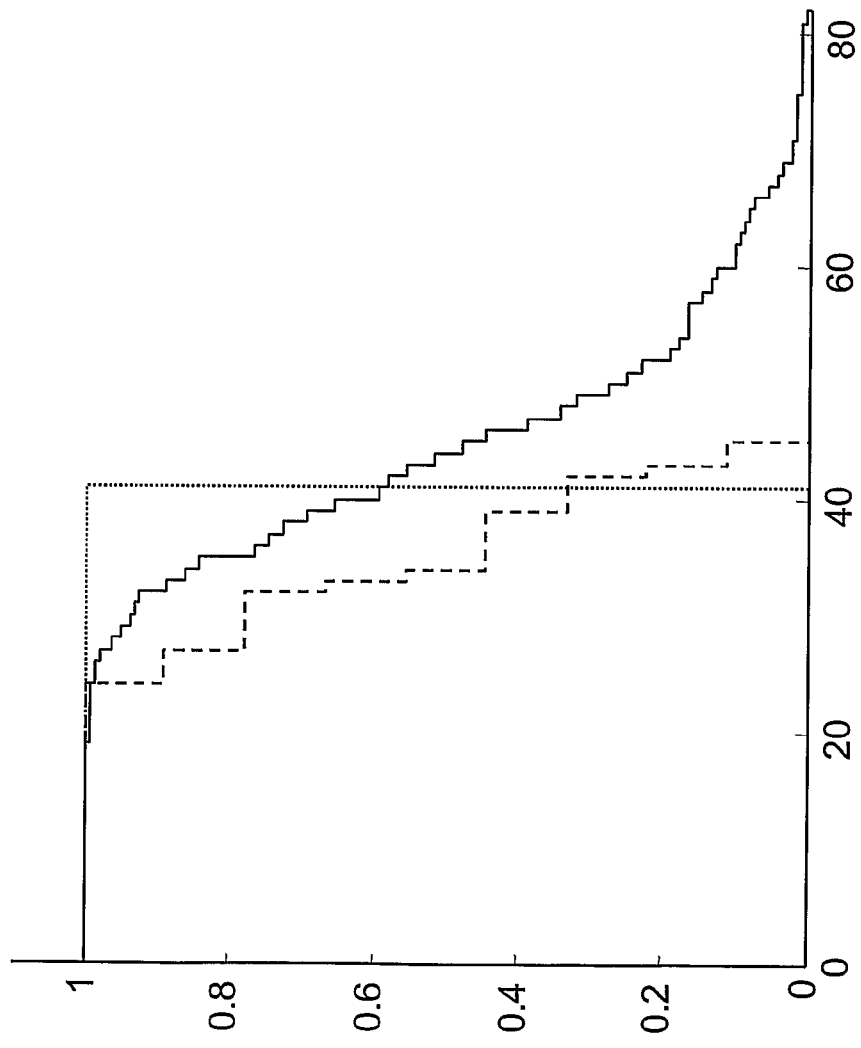

According to the Kaplan-Meier analysis, the median age at which BRCA1-carrying subjects bearing the AA, GA and GG genotypes at the rs28674628 SNP are diagnosed with breast cancer is 44, 34 and 41 years, respectively (p=0.00082 AA vs. GG). A Kaplan-Meier plot depicting these results is presented in FIG. 3D. Accordingly, at the rs28674628 SNP, the homozygous AA genotype was associated with a decreased risk of developing breast cancer among BRCA1 carriers.

7.d The rs2910164 SNP (in SEQ ID NO: 132)

The allele distribution at the rs2910164 SNP among the tested BRCA1 and BRCA2 carriers is presented in Table 15 as follows:

TABLE 15

Distribution of rs2910164 genotypes

|  |  | rs2910164 genotype | | | |
|---|---|---|---|---|---|
|  |  | GG | CG | CC | Total |
| BRCA1 | asymptomatic | 95 | 64 | 12 | 171 |
|  | breast cancer | 107 | 46 | 7 | 160 |
|  | ovarian cancer | 51 | 21 | 3 | 75 |
|  | Total | 253 | 131 | 22 | 406 |
| BRCA2 | asymptomatic | 35 | 17 | 2 | 54 |
|  | breast cancer | 49 | 23 | 2 | 74 |
|  | ovarian cancer | 15 | 6 | 0 | 21 |
|  | Total | 99 | 46 | 4 | 149 |
|  | Total | 352 | 177 | 26 | 555 |

Figure 3E:
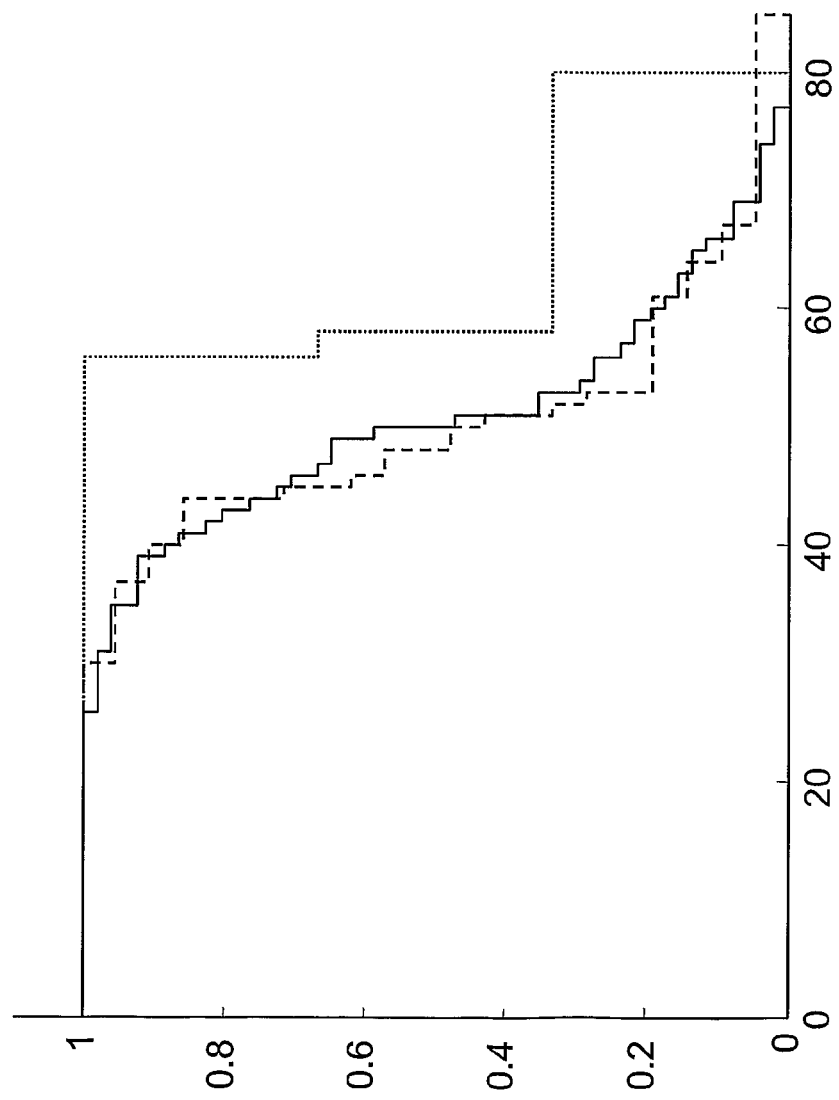

According to the Kaplan-Meier analysis, the median age at which BRCA1-carrying subjects bearing the GG, CG and CC genotypes at the rs2910164 SNP are diagnosed with ovarian cancer is 50, 48 and 58 years, respectively. A Kaplan-Meier plot depicting these results is presented in FIG. 3E. Accordingly, at the rs2910164 SNP, the homozygous CC genotype was associated with a decreased risk of developing ovarian cancer among BRCA1 carriers.

Figure 3F:
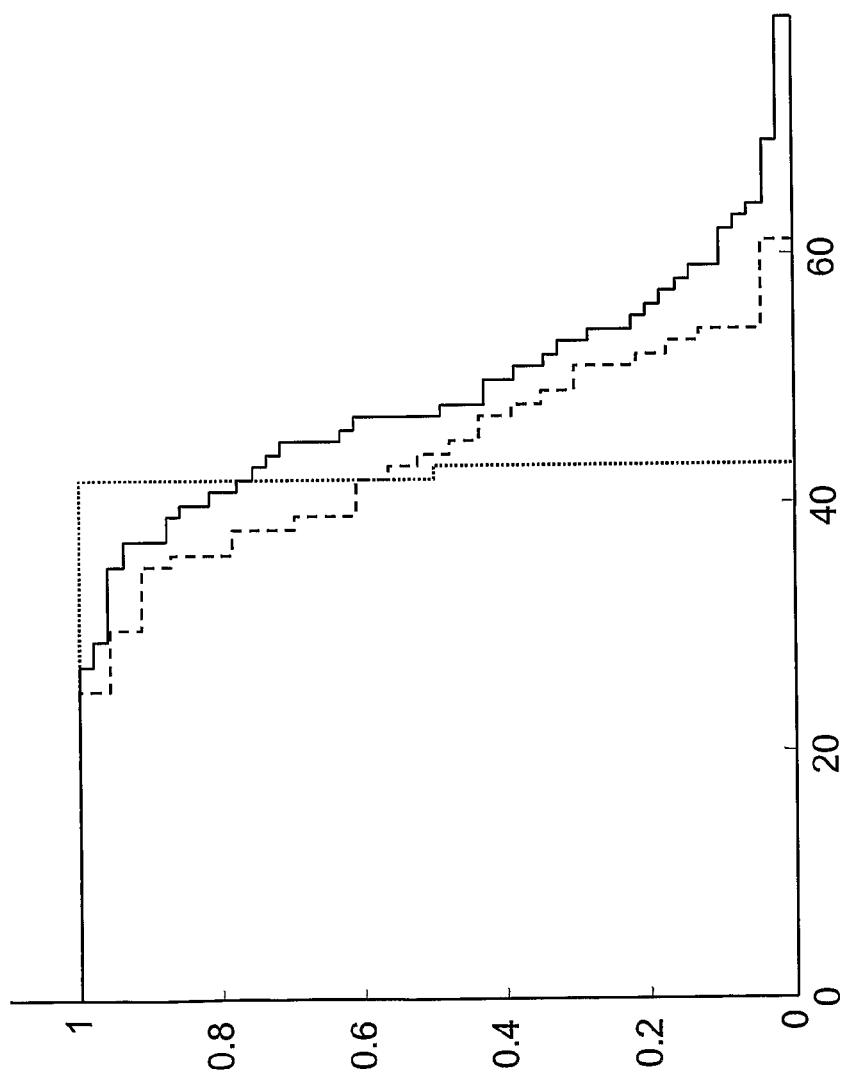

According to the Kaplan-Meier analysis, the median age at which BRCA2-carrying subjects bearing the GG, CG and CC genotypes at the rs2910164 SNP are diagnosed with breast cancer is 47, 44 and 42 years, respectively (p=0.054 GG vs. CC). A Kaplan-Meier plot depicting these results is presented in FIG. 3F. Accordingly, at the rs2910164 SNP, the homozygous GG genotype was associated with a decreased risk of developing breast cancer among BRCA2 carriers.

7.e The rs35664313 SNP (in SEQ ID NO: 105)

The allele distribution at the rs35664313 SNP among the tested BRCA1 and BRCA2 carriers is presented in Table 16 as follows:

TABLE 16

Distribution of rs35664313 genotypes

|  |  | rs35664313 genotype | | | |
|---|---|---|---|---|---|
|  |  | GG | G.DEL | DEL.DEL | Total |
| BRCA1 | asymptomatic | 58 | 88 | 40 | 186 |
|  | breast cancer | 57 | 76 | 31 | 164 |
|  | ovarian cancer | 29 | 31 | 17 | 77 |
|  | Total | 144 | 195 | 88 | 427 |
| BRCA2 | asymptomatic | 14 | 29 | 14 | 57 |
|  | breast cancer | 25 | 40 | 16 | 81 |
|  | ovarian cancer | 5 | 8 | 5 | 18 |
|  | Total | 44 | 77 | 35 | 156 |
|  | Total | 188 | 272 | 123 | 583 |

Figure 3G:
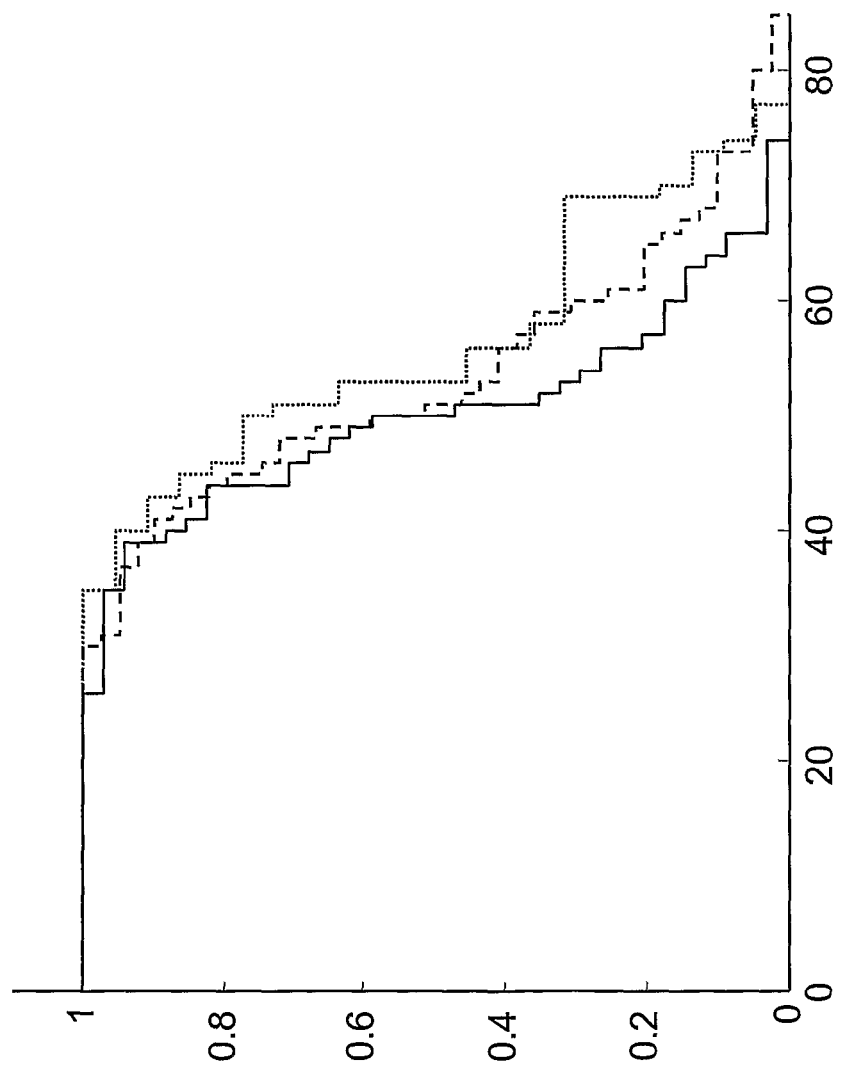

According to the Kaplan-Meier analysis, the median age at which the combined group of BRCA1- and BRCA2-carrying subjects bearing the GG, G.DEL and DEL.DEL genotypes at the rs35664313 SNP are diagnosed with ovarian cancer is 50, 51 and 53 years, respectively (p=0.035 GG vs. DEL.DEL). A Kaplan-Meier plot depicting these results is presented in FIG. 3G. Accordingly, at the rs35664313 SNP, the homozygous GG genotype was associated with an increased risk of developing ovarian cancer among BRCA1/2 carriers.

Figure 3H:
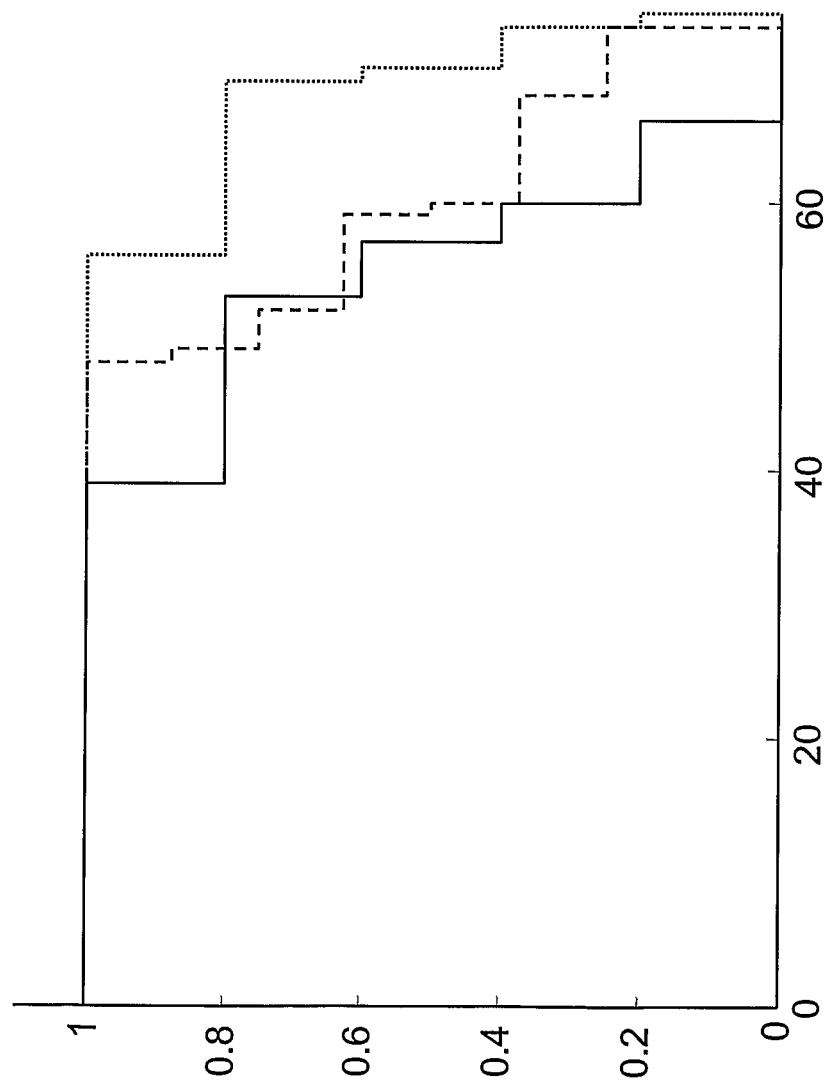

According to the Kaplan-Meier analysis, the median age at which BRCA2-carrying subjects bearing the GG, G.DEL and DEL.DEL genotypes at the rs35664313 SNP are diagnosed with ovarian cancer is 57, 59 and 70 years, respectively (p=0.040 GG vs. DEL.DEL). A Kaplan-Meier plot depicting these results is presented in FIG. 3H. Accordingly, at the rs35664313 SNP, the homozygous GG genotype was associated with an increased risk of developing ovarian cancer among BRCA2 carriers.

7.f The rs895819 SNP (in SEQ ID NO: 25)

The allele distribution at the rs895819 SNP among the tested BRCA1 and BRCA2 carriers is presented in Table 17 as follows:

TABLE 17

Distribution of rs895819 genotypes

| | | rs895819 genotype | | | |
|---|---|---|---|---|---|
| | | TT | CT | CC | Total |
| BRCA1 | asymptomatic | 94 | 67 | 16 | 177 |
| | breast cancer | 74 | 65 | 12 | 151 |
| | ovarian cancer | 43 | 29 | 2 | 74 |
| | Total | 211 | 161 | 30 | 402 |
| BRCA2 | asymptomatic | 32 | 22 | 2 | 56 |
| | breast cancer | 51 | 26 | 3 | 80 |
| | ovarian cancer | 8 | 9 | 2 | 19 |
| | Total | 91 | 57 | 7 | 155 |
| | Total | 302 | 218 | 37 | 557 |

Figure 3I:
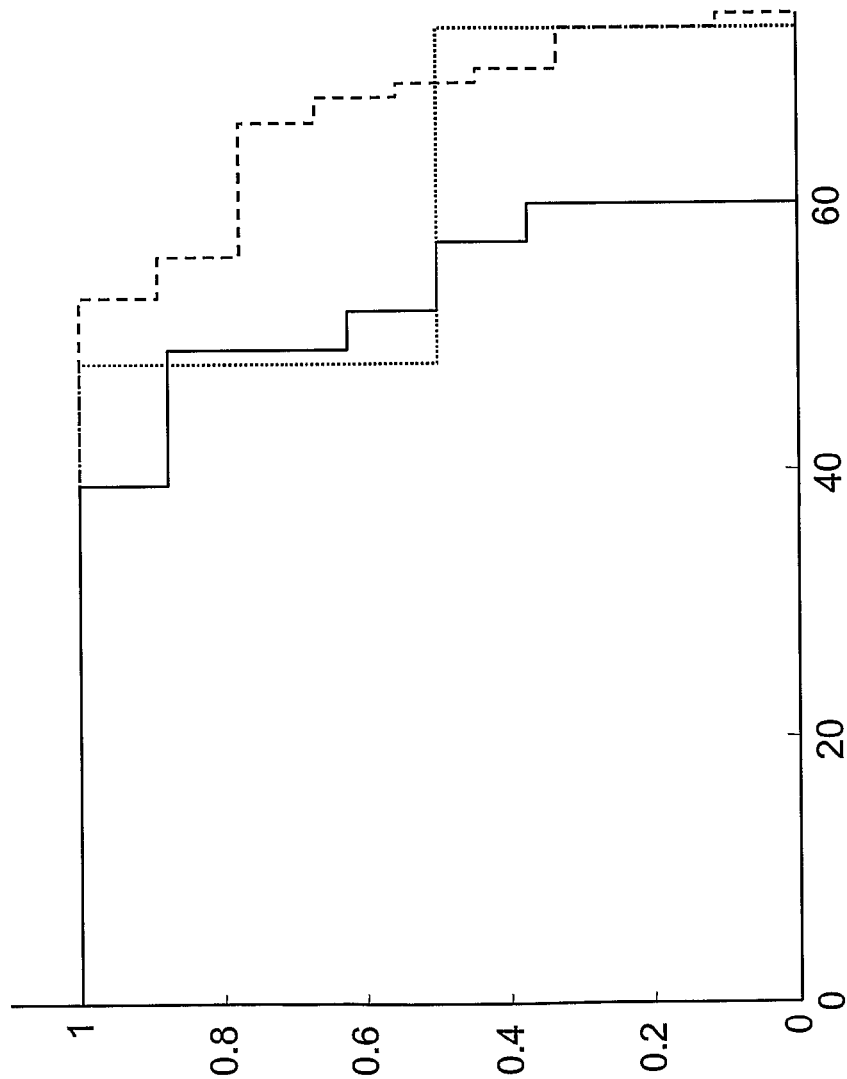

According to the Kaplan-Meier analysis, the median age at which BRCA2-carrying subjects bearing the TT, CT and CC genotypes at the rs895819 SNP are diagnosed with ovarian cancer is 52, 69 and 48 years, respectively (p=0.0092 TT vs. CT). A Kaplan-Meier plot depicting these results is presented in FIG. 3I. Accordingly, at the rs895819 SNP, the homozygous TT genotype was associated with an increased risk of developing ovarian cancer among BRCA2 carriers.

The results shown here correlate with the results obtained for the same SNP shown and discussed in Example 5e. Specifically, TT homozygotes have an increased risk of developing ovarian cancer, while the CT heterozygote has a decreased risk of developing ovarian cancer.

7.g The rs1042992 SNP (in SEQ ID NO: 90)

The allele distribution at the rs1042992 SNP among the tested BRCA1 and BRCA2 carriers is presented in Table 18 as follows:

TABLE 18

Distribution of rs1042992 genotypes

| | | rs1042992 genotype | | | |
|---|---|---|---|---|---|
| | | CC | CT | TT | Total |
| BRCA1 | asymptomatic | 132 | 39 | 1 | 172 |
| | breast cancer | 121 | 38 | 5 | 164 |
| | ovarian cancer | 14 | 56 | 2 | 72 |
| | Total | 267 | 133 | 8 | 408 |
| BRCA2 | asymptomatic | 33 | 17 | 0 | 50 |
| | breast cancer | 55 | 18 | 4 | 77 |
| | ovarian cancer | 17 | 4 | 0 | 21 |
| | Total | 105 | 39 | 4 | 148 |
| | Total | 414 | 130 | 12 | 556 |

According to the Kaplan-Meier analysis, the median age at which BRCA2-carrying subjects bearing the CC, CT and TT genotypes at the rs1042992 SNP are diagnosed with breast cancer is 47, 41 and 53 years, respectively. Accordingly, at the rs1042992 SNP, the homozygous TT genotype was associated with a decreased risk of developing breast cancer among BRCA2 carriers.

7.h The rs1056930 SNP (in SEQ ID NO: 91)

The allele distribution at the rs1056930 SNP among the tested BRCA1 and BRCA2 carriers is presented in Table 19 as follows:

TABLE 19

Distribution of rs1056930 genotypes

| | | rs1056930 genotype | | | |
|---|---|---|---|---|---|
| | | GG | GA | AA | Total |
| BRCA1 | asymptomatic | 67 | 70 | 34 | 171 |
| | breast cancer | 56 | 70 | 30 | 156 |
| | ovarian cancer | 24 | 37 | 9 | 70 |
| | Total | 147 | 177 | 73 | 397 |
| BRCA2 | asymptomatic | 17 | 25 | 8 | 50 |
| | breast cancer | 25 | 26 | 8 | 59 |
| | ovarian cancer | 5 | 9 | 4 | 18 |
| | Total | 47 | 60 | 20 | 127 |
| | Total | 194 | 237 | 93 | 524 |

According to the Kaplan-Meier analysis, the median age at which BRCA1-carrying subjects bearing the GG, GA and AA genotypes at the rs1056930 SNP are diagnosed with ovarian cancer is 54, 50 and 49 years, respectively (p=0.017 GG vs. AA). Accordingly, at the rs1056930 SNP, the homozygous GG genotype was associated with a decreased risk of developing ovarian cancer among BRCA1 carriers relative to the other genotypes.

7.i The rs1621 SNP (in SEQ ID NOS: 95-96)

The allele distribution at the rs1621 SNP among the tested BRCA1 and BRCA2 carriers is presented in Table 20 as follows:

TABLE 20

Distribution of rs1621 genotypes

| | | rs1621 genotype | | | |
|---|---|---|---|---|---|
| | | AA | GA | GG | Total |
| BRCA1 | asymptomatic | 79 | 79 | 16 | 174 |
| | breast cancer | 77 | 67 | 9 | 153 |
| | ovarian cancer | 35 | 29 | 9 | 73 |
| | Total | 191 | 175 | 34 | 400 |
| BRCA2 | asymptomatic | 37 | 19 | 3 | 59 |
| | breast cancer | 37 | 34 | 8 | 79 |
| | ovarian cancer | 4 | 12 | 4 | 20 |
| | Total | 78 | 65 | 15 | 158 |
| | Total | 269 | 240 | 49 | 558 |

According to the Kaplan-Meier analysis, the median age at which the combined group of BRCA1- and BRCA2-carrying subjects bearing the AA, GA and GG genotypes at the rs1621 SNP are diagnosed with ovarian cancer is 50, 51 and 53 years, respectively. Accordingly, at the rs1621 SNP, the homozygous AA genotype was associated with an increased risk of developing ovarian cancer among BRCA1/2 carriers.

7.j The rs2289047 SNP (in SEQ ID NO: 102)

The allele distribution at the rs2289047 SNP among the tested BRCA1 and BRCA2 carriers is presented in Table 21 as follows:

TABLE 21

Distribution of rs2289047 genotypes

|  |  | rs2289047 genotype | | | |
|---|---|---|---|---|---|
|  |  | GG | GT | TT | Total |
| BRCA1 | asymptomatic | 41 | 16 | 3 | 60 |
|  | breast cancer | 47 | 12 | 5 | 64 |
|  | ovarian cancer | 23 | 11 | 4 | 38 |
|  | Total | 111 | 39 | 12 | 162 |
| BRCA2 | asymptomatic | 33 | 6 | 2 | 41 |
|  | breast cancer | 30 | 10 | 2 | 42 |
|  | ovarian cancer | 6 | 1 | 0 | 7 |
|  | Total | 69 | 17 | 4 | 90 |
|  | Total | 180 | 56 | 16 | 252 |

According to the Kaplan-Meier analysis, the median age at which the combined group of BRCA1- and BRCA2-carrying subjects bearing the GG, GT and TT genotypes at the rs2289047 SNP are diagnosed with ovarian cancer is 51, 51 and 43 years, respectively. Accordingly, at the rs2289047 SNP, the homozygous TT genotype was associated with an increased risk of developing ovarian cancer among BRCA1/2 carriers.

7.k The rs3763763 SNP (in SEQ ID NO: 98)

The allele distribution at the rs3763763 SNP among the tested BRCA1 and BRCA2 carriers is presented in Table 22 as follows:

TABLE 22

Distribution of rs3763763 genotypes

|  |  | rs3763763 genotype | | | |
|---|---|---|---|---|---|
|  |  | CC | CA | AA | Total |
| BRCA1 | asymptomatic | 98 | 62 | 12 | 172 |
|  | breast cancer | 79 | 59 | 16 | 154 |
|  | ovarian cancer | 43 | 24 | 6 | 73 |
|  | Total | 220 | 145 | 34 | 399 |
| BRCA2 | asymptomatic | 26 | 30 | 5 | 61 |
|  | breast cancer | 38 | 33 | 5 | 76 |
|  | ovarian cancer | 12 | 7 | 1 | 20 |
|  | Total | 76 | 70 | 11 | 157 |
|  | Total | 296 | 215 | 45 | 556 |

According to the Kaplan-Meier analysis, the median age at which BRCA2-carrying subjects bearing the CC, CA and AA genotypes at the rs3763763 SNP are diagnosed with ovarian cancer is 60, 52 and 59 years, respectively (p=0.053 CC vs. AA). Accordingly, at the rs3763763 SNP, the homozygous CC genotype was associated with a decreased risk of developing ovarian cancer among BRCA2 carriers.

7.l The rs7085 SNP (in SEQ ID NO: 99-100)

The allele distribution at the rs7085 SNP among the tested BRCA1 and BRCA2 carriers is presented in Table 23 as follows:

TABLE 23

Distribution of rs7085 genotypes

|  |  | rs7085 genotype | | | |
|---|---|---|---|---|---|
|  |  | CC | CT | TT | Total |
| BRCA1 | asymptomatic | 84 | 31 | 15 | 130 |
|  | breast cancer | 78 | 41 | 11 | 130 |
|  | ovarian cancer | 28 | 29 | 7 | 64 |
|  | Total | 190 | 101 | 33 | 324 |
| BRCA2 | asymptomatic | 21 | 20 | 4 | 45 |
|  | breast cancer | 30 | 26 | 7 | 63 |
|  | ovarian cancer | 9 | 4 | 1 | 14 |
|  | Total | 60 | 50 | 12 | 122 |
|  | Total | 250 | 151 | 45 | 446 |

According to the Kaplan-Meier analysis, the median age at which the combined group of BRCA1- and BRCA2-carrying subjects bearing the CC, CT and TT genotypes at the rs7085 SNP are diagnosed with ovarian cancer is 48, 47 and 51 years, respectively. Accordingly, at the rs7085 SNP, the homozygous TT genotype was associated with a decreased risk of developing ovarian cancer among BRCA1/2 carriers.

7.m The rs8176318 SNP (in SEQ ID NO: 106-107)

The allele distribution at the rs8176318 SNP among the tested BRCA1 and BRCA2 carriers is presented in Table 24 as follows:

TABLE 24

Distribution of rs8176318 genotypes

|  |  | rs8176318 genotype | | | |
|---|---|---|---|---|---|
|  |  | GG | GT | TT | Total |
| BRCA1 | asymptomatic | 25 | 112 | 44 | 181 |
|  | breast cancer | 33 | 76 | 55 | 164 |
|  | ovarian cancer | 7 | 47 | 21 | 75 |
|  | Total | 65 | 235 | 120 | 420 |
| BRCA2 | asymptomatic | 25 | 29 | 4 | 58 |
|  | breast cancer | 39 | 34 | 7 | 80 |
|  | ovarian cancer | 7 | 9 | 1 | 17 |
|  | Total | 111 | 84 | 18 | 213 |
|  | Total | 136 | 307 | 132 | 575 |

According to the Kaplan-Meier analysis, the median age at which the combined group of BRCA1- and BRCA2-carrying subjects bearing the GG, GT and TT genotypes at the rs8176318 SNP are diagnosed with ovarian cancer is 53, 51 and 51 years, respectively (p=0.056 GG vs. TT). Accordingly, at the rs8176318 SNP, the homozygous GG genotype was associated with a decreased risk of developing ovarian cancer among BRCA1/2 carriers.

7.n The rs868 SNP (in SEQ ID NO: 101)

The allele distribution at the rs868 SNP among the tested BRCA1 and BRCA2 carriers is presented in Table 25 as follows:

TABLE 25

Distribution of rs868 genotypes

|   |   | rs868 genotype | | | |
|---|---|---|---|---|---|
|   |   | AA | GA | GG | Total |
| BRCA1 | asymptomatic | 115 | 57 | 3 | 175 |
|   | breast cancer | 99 | 48 | 3 | 150 |
|   | ovarian cancer | 53 | 19 | 0 | 72 |
|   | Total | 267 | 124 | 6 | 397 |
| BRCA2 | asymptomatic | 48 | 7 | 2 | 57 |
|   | breast cancer | 57 | 18 | 0 | 75 |
|   | ovarian cancer | 15 | 4 | 1 | 20 |
|   | Total | 120 | 29 | 3 | 152 |
|   | Total | 387 | 153 | 9 | 549 |

According to the Kaplan-Meier analysis, the median age at which the combined group of BRCA1- and BRCA2-carrying subjects bearing the AA, GA and GG genotypes at the rs868 SNP are diagnosed with ovarian cancer is 51, 53 and 66 years, respectively. Accordingly, at the rs868 SNP, the homozygous AA genotype was associated with an increased risk of developing ovarian cancer among BRCA1/2 carriers.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A method for detecting a risk of developing breast or ovarian cancer in a human subject carrying a BRCA2 mutation comprising detecting a nucleic acid sequence of a polymorphism of a microRNA-related gene or variant thereof comprising SEQ ID NO: 1 by nucleic acid amplification or extension using any one of SEQ ID NO: 26, SEQ ID NO: 42 or SEQ ID NO: 58 as a primer, comparing the polymorphic pattern of the microRNA-related gene or variant thereof to a reference wild-type allele in a human subject not carrying the BRCA2 mutation, wherein the presence of a C/T heterozygote genotype at the rs11169571 SNP in said microRNA-related gene or variant thereof relative to the reference wild-type allele is indicative of an increased risk of developing breast or ovarian cancer in said human subject, and determining whether the human subject has an increased risk of developing breast or ovarian cancer based on the presence of the C/T heterozygote genotype at the rs11169571 SNP in the microRNA-related gene or variant thereof relative to the reference wild-type allele.

2. The method of claim 1, wherein said microRNA-related gene is selected from the group consisting of genes encoding a microRNA, a microRNA precursor, a mature miRNA and a microRNA target gene; and a gene involved in microRNA processing.

3. The method of claim 1, wherein said variation in microRNA-related gene is in a microRNA binding site within the 3' UTR of a microRNA target gene.

4. The method of claim 1, wherein any one of said primers is SEQ ID NO: 26.

5. The method of claim 1, wherein any one of said primers is SEQ ID NO: 42.

6. The method of claim 1, wherein said nucleic acid extension method comprises use of a primer of SEQ ID NO: 58.

* * * * *

SEQUENCE LISTING

<160> NUMBER OF SEQ ID NOS: 199

<210> SEQ ID NO 1
<211> LENGTH: 23
<212> TYPE: DNA
<213> ORGANISM: Homo sapiens

<400> SEQUENCE: 1
tacgggcaca actggaagct ttg                                              23

<210> SEQ ID NO 2
<211> LENGTH: 22
<212> TYPE: DNA
<213> ORGANISM: Homo sapiens

<400> SEQUENCE: 2
ggcacaactg gaagctttgt ag                                               22

<210> SEQ ID NO 3
<211> LENGTH: 21
<212> TYPE: DNA
<213> ORGANISM: Homo sapiens

<400> SEQUENCE: 3
cgggcacaac tggaagcttt g                                                21

<210> SEQ ID NO 4
<211> LENGTH: 18
<212> TYPE: DNA
<213> ORGANISM: Homo sapiens

<400> SEQUENCE: 4
cgggcacaac tggaagct                                                    18

<210> SEQ ID NO 5
<211> LENGTH: 23
<212> TYPE: DNA
<213> ORGANISM: Homo sapiens

<400> SEQUENCE: 5
acgggcacaa ctggaagctt tgt                                              23

```
<210> SEQ ID NO 6
<211> LENGTH: 23
<212> TYPE: DNA
<213> ORGANISM: Homo sapiens

<400> SEQUENCE: 6
ggcacaactg gaagctttgt aga                                              23

<210> SEQ ID NO 7
<211> LENGTH: 21
<212> TYPE: DNA
<213> ORGANISM: Homo sapiens

<400> SEQUENCE: 7
gcccaccttc agcctgcaat g                                                21

<210> SEQ ID NO 8
<211> LENGTH: 21
<212> TYPE: DNA
<213> ORGANISM: Homo sapiens

<400> SEQUENCE: 8 tttctctat tctctgcaat t                                                 21

<210> SEQ ID NO 9
<211> LENGTH: 23
<212> TYPE: DNA
<213> ORGANISM: Homo sapiens

<400> SEQUENCE: 9
cgcagcccgc aggcagcccc aca                                              23

<210> SEQ ID NO 10
<211> LENGTH: 22
<212> TYPE: DNA
<213> ORGANISM: Homo sapiens

<400> SEQUENCE: 10
taatggaatg tgagagttta ct                                               22

<210> SEQ ID NO 11
<211> LENGTH: 20
<212> TYPE: DNA
<213> ORGANISM: Homo sapiens

<400> SEQUENCE: 11
atggaatgtg agagtttact                                                  20

<210> SEQ ID NO 12
<211> LENGTH: 24
<212> TYPE: DNA
<213> ORGANISM: Homo sapiens

<400> SEQUENCE: 12
gttgcttccc caaaccacac tttt                                             24

<210> SEQ ID NO 13
<211> LENGTH: 21
<212> TYPE: DNA
<213> ORGANISM: Homo sapiens

<400> SEQUENCE: 13
gcttccccaa accacacttt t                                                21
```

<210> SEQ ID NO 14
<211> LENGTH: 21
<212> TYPE: DNA
<213> ORGANISM: Homo sapiens

<400> SEQUENCE: 14
ggtgctggga ctgagccagt c                                      21

<210> SEQ ID NO 15
<211> LENGTH: 22
<212> TYPE: DNA
<213> ORGANISM: Homo sapiens

<400> SEQUENCE: 15
tactgctggg tataatgcaa tg                                     22

<210> SEQ ID NO 16
<211> LENGTH: 21
<212> TYPE: DNA
<213> ORGANISM: Homo sapiens

<400> SEQUENCE: 16
actgctgggt ataatgcaat g                                      21

<210> SEQ ID NO 17
<211> LENGTH: 21
<212> TYPE: DNA
<213> ORGANISM: Homo sapiens

<400> SEQUENCE: 17
actgctgggt ataatgcaat g                                      21

<210> SEQ ID NO 18
<211> LENGTH: 21
<212> TYPE: DNA
<213> ORGANISM: Homo sapiens

<400> SEQUENCE: 18
actgctgggt ataatgcaat g                                      21

<210> SEQ ID NO 19
<211> LENGTH: 20
<212> TYPE: DNA
<213> ORGANISM: Homo sapiens

<400> SEQUENCE: 19
ttgcagaatc tgcccagagt                                        20

<210> SEQ ID NO 20
<211> LENGTH: 22
<212> TYPE: DNA
<213> ORGANISM: Homo sapiens

<400> SEQUENCE: 20
aaatgttttt aaagaagcca gc                                     22

<210> SEQ ID NO 21
<211> LENGTH: 22
<212> TYPE: DNA
<213> ORGANISM: Homo sapiens

<400> SEQUENCE: 21
gcgccagtca tttgctccgt tt                                     22

<210> SEQ ID NO 22
<211> LENGTH: 110
<212> TYPE: DNA
<213> ORGANISM: Homo sapiens

<400> SEQUENCE: 22
tgctcgctca gctgatctgt ggcttaggta gtttcatgtt gttgggattg agttttgaac     60
tcggcaacaa gaaactgcct gagttacatc agtcggtttt cgtcgagggc                110

<210> SEQ ID NO 23
<211> LENGTH: 94
<212> TYPE: DNA
<213> ORGANISM: Homo sapiens

<400> SEQUENCE: 23
ataaaggaag ttaggctgag gggcagagag cgagactttt ctattttcca aaagctcggt     60
ctgaggcccc tcagtcttgc ttcctaaccc gcgc                                 94

<210> SEQ ID NO 24
<211> LENGTH: 89
<212> TYPE: DNA
<213> ORGANISM: Homo sapiens

<400> SEQUENCE: 24
gccggcgccc gagctctggc tccgtgtctt cactcccgtg cttgtccgag gagggaggga     60
gggacggggg ctgtgctggg gcagctgga                                       89

<210> SEQ ID NO 25
<211> LENGTH: 78
<212> TYPE: DNA
<213> ORGANISM: Homo sapiens

<400> SEQUENCE: 25 ctgggggcg gaacttagcc actgtgaaca cgacttggtg tggaccctgc tcacaagcag      60
ctaagccctg ctcctcag                                                   78

<210> SEQ ID NO 26
<211> LENGTH: 30
<212> TYPE: DNA
<213> ORGANISM: Artificial sequence
<220> FEATURE:
<223> OTHER INFORMATION: Synthetic

<400> SEQUENCE: 26
acgttggatg atgacctcaa ggaagctacg                                      30

<210> SEQ ID NO 27
<211> LENGTH: 30
<212> TYPE: DNA
<213> ORGANISM: Artificial sequence
<220> FEATURE:
<223> OTHER INFORMATION: Synthetic

<400> SEQUENCE: 27
acgttggatg gaagggacaa gactatgtgc                                      30

<210> SEQ ID NO 28
<211> LENGTH: 29
<212> TYPE: DNA
<213> ORGANISM: Artificial sequence
<220> FEATURE:

-continued

<223> OTHER INFORMATION: Synthetic

<400> SEQUENCE: 28
acgttggatg cctctaagta catatgtag                               29

<210> SEQ ID NO 29
<211> LENGTH: 30
<212> TYPE: DNA
<213> ORGANISM: Artificial sequence
<220> FEATURE:
<223> OTHER INFORMATION: Synthetic

<400> SEQUENCE: 29
acgttggatg agctggagaa ctactgcaac                              30

<210> SEQ ID NO 30
<211> LENGTH: 30
<212> TYPE: DNA
<213> ORGANISM: Artificial sequence
<220> FEATURE:
<223> OTHER INFORMATION: Synthetic

<400> SEQUENCE: 30
acgttggatg gaccatgaat gaatgtttcc                              30

<210> SEQ ID NO 31
<211> LENGTH: 30
<212> TYPE: DNA
<213> ORGANISM: Artificial sequence
<220> FEATURE:
<223> OTHER INFORMATION: Synthetic

<400> SEQUENCE: 31
acgttggatg ggactgcaga tgattctagg                              30

<210> SEQ ID NO 32
<211> LENGTH: 29
<212> TYPE: DNA
<213> ORGANISM: Artificial sequence
<220> FEATURE:
<223> OTHER INFORMATION: Synthetic

<400> SEQUENCE: 32
acgttggatg tccaggccaa tacatgccc                               29

<210> SEQ ID NO 33
<211> LENGTH: 30
<212> TYPE: DNA
<213> ORGANISM: Artificial sequence
<220> FEATURE:
<223> OTHER INFORMATION: Synthetic

<400> SEQUENCE: 33
acgttggatg ctgtcaattc tggcttctcc                              30

<210> SEQ ID NO 34
<211> LENGTH: 30
<212> TYPE: DNA
<213> ORGANISM: Artificial sequence
<220> FEATURE:
<223> OTHER INFORMATION: Synthetic

<400> SEQUENCE: 34
acgttggatg atcagtagta tgagcagcag                              30

-continued

```
<210> SEQ ID NO 35
<211> LENGTH: 30
<212> TYPE: DNA
<213> ORGANISM: Artificial sequence
<220> FEATURE:
<223> OTHER INFORMATION: Synthetic

<400> SEQUENCE: 35
acgttggatg acagtgagca caattagccg                                    30

<210> SEQ ID NO 36
<211> LENGTH: 30
<212> TYPE: DNA
<213> ORGANISM: Artificial sequence
<220> FEATURE:
<223> OTHER INFORMATION: Synthetic

<400> SEQUENCE: 36
acgttggatg aaggtttcaa agcgccagtc                                    30

<210> SEQ ID NO 37
<211> LENGTH: 30
<212> TYPE: DNA
<213> ORGANISM: Artificial sequence
<220> FEATURE:
<223> OTHER INFORMATION: Synthetic

<400> SEQUENCE: 37
acgttggatg ctgatctgtg gcttaggtag                                    30

<210> SEQ ID NO 38
<211> LENGTH: 30
<212> TYPE: DNA
<213> ORGANISM: Artificial sequence
<220> FEATURE:
<223> OTHER INFORMATION: Synthetic

<400> SEQUENCE: 38
acgttggatg actgtctctc ttcacactgc                                    30

<210> SEQ ID NO 39
<211> LENGTH: 28
<212> TYPE: DNA
<213> ORGANISM: Artificial sequence
<220> FEATURE:
<223> OTHER INFORMATION: Synthetic

<400> SEQUENCE: 39
acgttggatg ccggccaact cgcccagc                                      28

<210> SEQ ID NO 40
<211> LENGTH: 30
<212> TYPE: DNA
<213> ORGANISM: Artificial sequence
<220> FEATURE:
<223> OTHER INFORMATION: Synthetic

<400> SEQUENCE: 40
acgttggatg agggcttagc tgcttgtgag                                    30

<210> SEQ ID NO 41
<211> LENGTH: 30
<212> TYPE: DNA
<213> ORGANISM: Artificial sequence
<220> FEATURE:
<223> OTHER INFORMATION: Synthetic
```

<400> SEQUENCE: 41
acgttggatg ggaacttagc cactgtgaac                                              30

<210> SEQ ID NO 42
<211> LENGTH: 30
<212> TYPE: DNA
<213> ORGANISM: Artificial sequence
<220> FEATURE:
<223> OTHER INFORMATION: Synthetic

<400> SEQUENCE: 42
acgttggatg gaaagttcat ttcttgctcc                                              30

<210> SEQ ID NO 43
<211> LENGTH: 30
<212> TYPE: DNA
<213> ORGANISM: Artificial sequence
<220> FEATURE:
<223> OTHER INFORMATION: Synthetic

<400> SEQUENCE: 43
acgttggatg gaagggacaa gactatgtgc                                              30

<210> SEQ ID NO 44
<211> LENGTH: 29
<212> TYPE: DNA
<213> ORGANISM: Artificial sequence
<220> FEATURE:
<223> OTHER INFORMATION: Synthetic

<400> SEQUENCE: 44
acgttggatg cctctaagta catatgtag                                               29

<210> SEQ ID NO 45
<211> LENGTH: 30
<212> TYPE: DNA
<213> ORGANISM: Artificial sequence
<220> FEATURE:
<223> OTHER INFORMATION: Synthetic

<400> SEQUENCE: 45
acgttggatg agctggagaa ctactgcaac                                              30

<210> SEQ ID NO 46
<211> LENGTH: 30
<212> TYPE: DNA
<213> ORGANISM: Artificial sequence
<220> FEATURE:
<223> OTHER INFORMATION: Synthetic

<400> SEQUENCE: 46
acgttggatg gaccatgaat gaatgtttcc                                              30

<210> SEQ ID NO 47
<211> LENGTH: 30
<212> TYPE: DNA
<213> ORGANISM: Artificial sequence
<220> FEATURE:
<223> OTHER INFORMATION: Synthetic

<400> SEQUENCE: 47
acgttggatg ggactgcaga tgattctagg                                              30

<210> SEQ ID NO 48
<211> LENGTH: 29

-continued

<212> TYPE: DNA
<213> ORGANISM: Artificial sequence
<220> FEATURE:
<223> OTHER INFORMATION: Synthetic

<400> SEQUENCE: 48
acgttggatg tccaggccaa tacatgccc                                    29

<210> SEQ ID NO 49
<211> LENGTH: 30
<212> TYPE: DNA
<213> ORGANISM: Artificial sequence
<220> FEATURE:
<223> OTHER INFORMATION: Synthetic

<400> SEQUENCE: 49
acgttggatg ctgtcaattc tggcttctcc                                   30

<210> SEQ ID NO 50
<211> LENGTH: 30
<212> TYPE: DNA
<213> ORGANISM: Artificial sequence
<220> FEATURE:
<223> OTHER INFORMATION: Synthetic

<400> SEQUENCE: 50
acgttggatg atcagtagta tgagcagcag                                   30

<210> SEQ ID NO 51
<211> LENGTH: 30
<212> TYPE: DNA
<213> ORGANISM: Artificial sequence
<220> FEATURE:
<223> OTHER INFORMATION: Synthetic

<400> SEQUENCE: 51
acgttggatg acagtgagca caattagccg                                   30

<210> SEQ ID NO 52
<211> LENGTH: 30
<212> TYPE: DNA
<213> ORGANISM: Artificial sequence
<220> FEATURE:
<223> OTHER INFORMATION: Synthetic

<400> SEQUENCE: 52
acgttggatg aaggtttcaa agcgccagtc                                   30

<210> SEQ ID NO 53
<211> LENGTH: 30
<212> TYPE: DNA
<213> ORGANISM: Artificial sequence
<220> FEATURE:
<223> OTHER INFORMATION: Synthetic

<400> SEQUENCE: 53
acgttggatg ctgatctgtg gcttaggtag                                   30

<210> SEQ ID NO 54
<211> LENGTH: 30
<212> TYPE: DNA
<213> ORGANISM: Artificial sequence
<220> FEATURE:
<223> OTHER INFORMATION: Synthetic

<400> SEQUENCE: 54

```
acgttggatg actgtctctc ttcacactgc                                    30
```

<210> SEQ ID NO 55
<211> LENGTH: 28
<212> TYPE: DNA
<213> ORGANISM: Artificial sequence
<220> FEATURE:
<223> OTHER INFORMATION: Synthetic

<400> SEQUENCE: 55

```
acgttggatg ccggccaact cgcccagc                                      28
```

<210> SEQ ID NO 56
<211> LENGTH: 30
<212> TYPE: DNA
<213> ORGANISM: Artificial sequence
<220> FEATURE:
<223> OTHER INFORMATION: Synthetic

<400> SEQUENCE: 56

```
acgttggatg agggcttagc tgcttgtgag                                    30
```

<210> SEQ ID NO 57
<211> LENGTH: 30
<212> TYPE: DNA
<213> ORGANISM: Artificial sequence
<220> FEATURE:
<223> OTHER INFORMATION: Synthetic

<400> SEQUENCE: 57

```
acgttggatg ggaacttagc cactgtgaac                                    30
```

<210> SEQ ID NO 58
<211> LENGTH: 25
<212> TYPE: DNA
<213> ORGANISM: Artificial sequence
<220> FEATURE:
<223> OTHER INFORMATION: Synthetic

<400> SEQUENCE: 58

```
ccatctacgg gcacaactgg aagcc                                         25
```

<210> SEQ ID NO 59
<211> LENGTH: 25
<212> TYPE: DNA
<213> ORGANISM: Artificial sequence
<220> FEATURE:
<223> OTHER INFORMATION: Synthetic

<400> SEQUENCE: 59

```
ccatctacgg gcacaactgg aagct                                         25
```

<210> SEQ ID NO 60
<211> LENGTH: 19
<212> TYPE: DNA
<213> ORGANISM: Artificial sequence
<220> FEATURE:
<223> OTHER INFORMATION: Synthetic

<400> SEQUENCE: 60

```
cccaccttca gcctgcaac                                                19
```

<210> SEQ ID NO 61
<211> LENGTH: 19
<212> TYPE: DNA
<213> ORGANISM: Artificial sequence

```
<220> FEATURE:
<223> OTHER INFORMATION: Synthetic

<400> SEQUENCE: 61
cccaccttca gcctgcaat                                          19

<210> SEQ ID NO 62
<211> LENGTH: 26
<212> TYPE: DNA
<213> ORGANISM: Artificial sequence
<220> FEATURE:
<223> OTHER INFORMATION: Synthetic

<400> SEQUENCE: 62
gaacctattt ttttctctat tctctc                                  26

<210> SEQ ID NO 63
<211> LENGTH: 26
<212> TYPE: DNA
<213> ORGANISM: Artificial sequence
<220> FEATURE:
<223> OTHER INFORMATION: Synthetic

<400> SEQUENCE: 63
gaacctattt ttttctctat tctctg                                  26

<210> SEQ ID NO 64
<211> LENGTH: 24
<212> TYPE: DNA
<213> ORGANISM: Artificial sequence
<220> FEATURE:
<223> OTHER INFORMATION: Synthetic

<400> SEQUENCE: 64
cccccaagcc cgcaggcagc cccc                                    24

<210> SEQ ID NO 65
<211> LENGTH: 24
<212> TYPE: DNA
<213> ORGANISM: Artificial sequence
<220> FEATURE:
<223> OTHER INFORMATION: Synthetic

<400> SEQUENCE: 65
cccccaagcc cgcaggcagc ccca                                    24

<210> SEQ ID NO 66
<211> LENGTH: 25
<212> TYPE: DNA
<213> ORGANISM: Artificial sequence
<220> FEATURE:
<223> OTHER INFORMATION: Synthetic

<400> SEQUENCE: 66
gttctaatgg aatgtgagag tttac                                   25

<210> SEQ ID NO 67
<211> LENGTH: 25
<212> TYPE: DNA
<213> ORGANISM: Artificial sequence
<220> FEATURE:
<223> OTHER INFORMATION: Synthetic

<400> SEQUENCE: 67
gttctaatgg aatgtgagag tttat                                   25
```

<210> SEQ ID NO 68
<211> LENGTH: 25
<212> TYPE: DNA
<213> ORGANISM: Artificial sequence
<220> FEATURE:
<223> OTHER INFORMATION: Synthetic

<400> SEQUENCE: 68
gatgattcta ggttttgatt aaaac                                  25

<210> SEQ ID NO 69
<211> LENGTH: 25
<212> TYPE: DNA
<213> ORGANISM: Artificial sequence
<220> FEATURE:
<223> OTHER INFORMATION: Synthetic

<400> SEQUENCE: 69
gatgattcta ggttttgatt aaaag                                  25

<210> SEQ ID NO 70
<211> LENGTH: 24
<212> TYPE: DNA
<213> ORGANISM: Artificial sequence
<220> FEATURE:
<223> OTHER INFORMATION: Synthetic

<400> SEQUENCE: 70
aggccaatac atgcccctgg gacg                                   24

<210> SEQ ID NO 71
<211> LENGTH: 24
<212> TYPE: DNA
<213> ORGANISM: Artificial sequence
<220> FEATURE:
<223> OTHER INFORMATION: Synthetic

<400> SEQUENCE: 71
aggccaatac atgcccctgg gact                                   24

<210> SEQ ID NO 72
<211> LENGTH: 21
<212> TYPE: DNA
<213> ORGANISM: Artificial sequence
<220> FEATURE:
<223> OTHER INFORMATION: Synthetic

<400> SEQUENCE: 72
ccatgctcac actttcttcc a                                      21

<210> SEQ ID NO 73
<211> LENGTH: 21
<212> TYPE: DNA
<213> ORGANISM: Artificial sequence
<220> FEATURE:
<223> OTHER INFORMATION: Synthetic

<400> SEQUENCE: 73
ccatgctcac actttcttcc g                                      21

<210> SEQ ID NO 74
<211> LENGTH: 18
<212> TYPE: DNA
<213> ORGANISM: Artificial sequence
<220> FEATURE:
<223> OTHER INFORMATION: Synthetic

```
<400> SEQUENCE: 74
atgagcagca gctggacc                                                    18

<210> SEQ ID NO 75
<211> LENGTH: 18
<212> TYPE: DNA
<213> ORGANISM: Artificial sequence
<220> FEATURE:
<223> OTHER INFORMATION: Synthetic

<400> SEQUENCE: 75
atgagcagca gctggact                                                    18

<210> SEQ ID NO 76
<211> LENGTH: 27
<212> TYPE: DNA
<213> ORGANISM: Artificial sequence
<220> FEATURE:
<223> OTHER INFORMATION: Synthetic

<400> SEQUENCE: 76
tatagaaaat gttttttaaag aagccaa                                         27

<210> SEQ ID NO 77
<211> LENGTH: 27
<212> TYPE: DNA
<213> ORGANISM: Artificial sequence
<220> FEATURE:
<223> OTHER INFORMATION: Synthetic

<400> SEQUENCE: 77
tatagaaaat gttttttaaag aagccag                                         27

<210> SEQ ID NO 78
<211> LENGTH: 17
<212> TYPE: DNA
<213> ORGANISM: Artificial sequence
<220> FEATURE:
<223> OTHER INFORMATION: Synthetic

<400> SEQUENCE: 78
cgccagtcat ttgctcc                                                     17

<210> SEQ ID NO 79
<211> LENGTH: 17
<212> TYPE: DNA
<213> ORGANISM: Artificial sequence
<220> FEATURE:
<223> OTHER INFORMATION: Synthetic

<400> SEQUENCE: 79
cgccagtcat ttgctct                                                     17

<210> SEQ ID NO 80
<211> LENGTH: 18
<212> TYPE: DNA
<213> ORGANISM: Artificial sequence
<220> FEATURE:
<223> OTHER INFORMATION: Synthetic

<400> SEQUENCE: 80
tcggcaacaa gaaactgc                                                    18

<210> SEQ ID NO 81
```

```
<211> LENGTH: 18
<212> TYPE: DNA
<213> ORGANISM: Artificial sequence
<220> FEATURE:
<223> OTHER INFORMATION: Synthetic

<400> SEQUENCE: 81
tcggcaacaa gaaactgt                                                    18

<210> SEQ ID NO 82
<211> LENGTH: 26
<212> TYPE: DNA
<213> ORGANISM: Artificial sequence
<220> FEATURE:
<223> OTHER INFORMATION: Synthetic

<400> SEQUENCE: 82
gagcggggag aaactcaagc gcgggg                                           26

<210> SEQ ID NO 83
<211> LENGTH: 26
<212> TYPE: DNA
<213> ORGANISM: Artificial sequence
<220> FEATURE:
<223> OTHER INFORMATION: Synthetic

<400> SEQUENCE: 83
gagcggggag aaactcaagc gcgggt                                           26

<210> SEQ ID NO 84
<211> LENGTH: 23
<212> TYPE: DNA
<213> ORGANISM: Artificial sequence
<220> FEATURE:
<223> OTHER INFORMATION: Synthetic

<400> SEQUENCE: 84
gccaggcgac ctgcgttgtt cca                                              23

<210> SEQ ID NO 85
<211> LENGTH: 23
<212> TYPE: DNA
<213> ORGANISM: Artificial sequence
<220> FEATURE:
<223> OTHER INFORMATION: Synthetic

<400> SEQUENCE: 85
gccaggcgac ctgcgttgtt ccg                                              23

<210> SEQ ID NO 86
<211> LENGTH: 17
<212> TYPE: DNA
<213> ORGANISM: Artificial sequence
<220> FEATURE:
<223> OTHER INFORMATION: Synthetic

<400> SEQUENCE: 86
tgcttgtgag cagggtc                                                     17

<210> SEQ ID NO 87
<211> LENGTH: 17
<212> TYPE: DNA
<213> ORGANISM: Artificial sequence
<220> FEATURE:
<223> OTHER INFORMATION: Synthetic

<400> SEQUENCE: 87
```
tgcttgtgag cagggtt                                                   17

<210> SEQ ID NO 88
<211> LENGTH: 20
<212> TYPE: DNA
<213> ORGANISM: Artificial sequence
<220> FEATURE:
<223> OTHER INFORMATION: Synthetic

<400> SEQUENCE: 88
cactgtgaac acgacttggc                                                20

<210> SEQ ID NO 89
<211> LENGTH: 20
<212> TYPE: DNA
<213> ORGANISM: Artificial sequence
<220> FEATURE:
<223> OTHER INFORMATION: Synthetic

<400> SEQUENCE: 89
cactgtgaac acgacttggt                                                20

<210> SEQ ID NO 90
<211> LENGTH: 23
<212> TYPE: DNA
<213> ORGANISM: Homo sapiens

<400> SEQUENCE: 90
ttcgttcatt tctaaaatgt gaa                                            23

<210> SEQ ID NO 91
<211> LENGTH: 23
<212> TYPE: DNA
<213> ORGANISM: Homo sapiens

<400> SEQUENCE: 91
atgcatcaga taacaactgt gag                                            23

<210> SEQ ID NO 92
<211> LENGTH: 23
<212> TYPE: DNA
<213> ORGANISM: Homo sapiens

<400> SEQUENCE: 92
tgccaaattt ttctgaatgt gac                                            23

<210> SEQ ID NO 93
<211> LENGTH: 23
<212> TYPE: DNA
<213> ORGANISM: Homo sapiens

<400> SEQUENCE: 93
tgacttatgt cttacttgcc aaa                                            23

<210> SEQ ID NO 94
<211> LENGTH: 23
<212> TYPE: DNA
<213> ORGANISM: Homo sapiens

<400> SEQUENCE: 94
cttgccaaat ttttctgaat gtg                                            23

<210> SEQ ID NO 95

```
<211> LENGTH: 25
<212> TYPE: DNA
<213> ORGANISM: Homo sapiens

<400> SEQUENCE: 95
tgtggaattt tgtgcttgct actgt                                          25

<210> SEQ ID NO 96
<211> LENGTH: 23
<212> TYPE: DNA
<213> ORGANISM: Homo sapiens

<400> SEQUENCE: 96
gaattttgtg cttgctactg tat                                            23

<210> SEQ ID NO 97
<211> LENGTH: 22
<212> TYPE: RNA
<213> ORGANISM: Homo sapiens

<400> SEQUENCE: 97
ugagguagua gguuguauag uu                                             22

<210> SEQ ID NO 98
<211> LENGTH: 23
<212> TYPE: DNA
<213> ORGANISM: Homo sapiens

<400> SEQUENCE: 98
ggacttaact gttgcgtgca ata                                            23

<210> SEQ ID NO 99
<211> LENGTH: 23
<212> TYPE: DNA
<213> ORGANISM: Homo sapiens

<400> SEQUENCE: 99
agatggaatt gtaataaacc acg                                            23

<210> SEQ ID NO 100
<211> LENGTH: 23
<212> TYPE: DNA
<213> ORGANISM: Homo sapiens

<400> SEQUENCE: 100
gagatggaat tgtaataaac cac                                            23

<210> SEQ ID NO 101
<211> LENGTH: 23
<212> TYPE: DNA
<213> ORGANISM: Homo sapiens

<400> SEQUENCE: 101
gggaggtcaa ttgttctacc tca                                            23

<210> SEQ ID NO 102
<211> LENGTH: 22
<212> TYPE: DNA
<213> ORGANISM: Homo sapiens

<400> SEQUENCE: 102
cttctcgatg tagatgttta tg                                             22
```

-continued

```
<210> SEQ ID NO 103
<211> LENGTH: 21
<212> TYPE: DNA
<213> ORGANISM: Homo sapiens

<400> SEQUENCE: 103
tattgttgga tactgaatga c                                          21

<210> SEQ ID NO 104
<211> LENGTH: 22
<212> TYPE: DNA
<213> ORGANISM: Homo sapiens

<400> SEQUENCE: 104
tggagaagtg agtgctcctt ga                                         22

<210> SEQ ID NO 105
<211> LENGTH: 22
<212> TYPE: DNA
<213> ORGANISM: Homo sapiens

<400> SEQUENCE: 105
caaagtaact taaacactgt ct                                         22

<210> SEQ ID NO 106
<211> LENGTH: 22
<212> TYPE: DNA
<213> ORGANISM: Homo sapiens

<400> SEQUENCE: 106
ttcacaaagg cagagagtca ga                                         22

<210> SEQ ID NO 107
<211> LENGTH: 23
<212> TYPE: DNA
<213> ORGANISM: Homo sapiens

<400> SEQUENCE: 107
gttcacaaag gcagagagtc aga                                        23

<210> SEQ ID NO 108
<211> LENGTH: 21
<212> TYPE: RNA
<213> ORGANISM: Homo sapiens

<400> SEQUENCE: 108
aucacauugc cagggauuuc c                                          21

<210> SEQ ID NO 109
<211> LENGTH: 21
<212> TYPE: RNA
<213> ORGANISM: Homo sapiens

<400> SEQUENCE: 109
aucacauugc cagggauuac c                                          21

<210> SEQ ID NO 110
<211> LENGTH: 21
<212> TYPE: RNA
<213> ORGANISM: Homo sapiens

<400> SEQUENCE: 110
uucacagugg cuaaguuccg c                                          21
```

```
<210> SEQ ID NO 111
<211> LENGTH: 21
<212> TYPE: RNA
<213> ORGANISM: Homo sapiens

<400> SEQUENCE: 111
uucacagugg cuaaguucug c                                              21

<210> SEQ ID NO 112
<211> LENGTH: 24
<212> TYPE: RNA
<213> ORGANISM: Homo sapiens

<400> SEQUENCE: 112
uuuggcaaug guagaacuca cacu                                           24

<210> SEQ ID NO 113
<211> LENGTH: 23
<212> TYPE: RNA
<213> ORGANISM: Homo sapiens

<400> SEQUENCE: 113
aacauucaac gcugucggug agu                                            23

<210> SEQ ID NO 114
<211> LENGTH: 23
<212> TYPE: RNA
<213> ORGANISM: Homo sapiens

<400> SEQUENCE: 114
aacauucauu gcugucggug ggu                                            23

<210> SEQ ID NO 115
<211> LENGTH: 22
<212> TYPE: RNA
<213> ORGANISM: Homo sapiens

<400> SEQUENCE: 115
acaguagucu gcacauuggu ua                                             22

<210> SEQ ID NO 116
<211> LENGTH: 21
<212> TYPE: RNA
<213> ORGANISM: Homo sapiens

<400> SEQUENCE: 116
uacaguacug ugauaacuga a                                              21

<210> SEQ ID NO 117
<211> LENGTH: 20
<212> TYPE: RNA
<213> ORGANISM: Homo sapiens

<400> SEQUENCE: 117
uacaguauag augauguacu                                                20

<210> SEQ ID NO 118
<211> LENGTH: 22
<212> TYPE: RNA
<213> ORGANISM: Homo sapiens

<400> SEQUENCE: 118
uagcagcaca uaaugguuug ug                                             22
```

```
<210> SEQ ID NO 119
<211> LENGTH: 22
<212> TYPE: RNA
<213> ORGANISM: Homo sapiens

<400> SEQUENCE: 119
cauugcacuu gucucggucu ga                                              22

<210> SEQ ID NO 120
<211> LENGTH: 22
<212> TYPE: RNA
<213> ORGANISM: Homo sapiens

<400> SEQUENCE: 120
uauugcacuu gucccggccu gu                                              22

<210> SEQ ID NO 121
<211> LENGTH: 22
<212> TYPE: RNA
<213> ORGANISM: Homo sapiens

<400> SEQUENCE: 121
cagugguuuu acccuauggu ag                                              22

<210> SEQ ID NO 122
<211> LENGTH: 22
<212> TYPE: RNA
<213> ORGANISM: Homo sapiens

<400> SEQUENCE: 122
ugguuuaccg ucccacauac au                                              22

<210> SEQ ID NO 123
<211> LENGTH: 22
<212> TYPE: RNA
<213> ORGANISM: Homo sapiens

<400> SEQUENCE: 123
uguaaacauc cucgacugga ag                                              22

<210> SEQ ID NO 124
<211> LENGTH: 22
<212> TYPE: RNA
<213> ORGANISM: Homo sapiens

<400> SEQUENCE: 124
uguaaacauc cccgacugga ag                                              22

<210> SEQ ID NO 125
<211> LENGTH: 22
<212> TYPE: RNA
<213> ORGANISM: Homo sapiens

<400> SEQUENCE: 125
uucauucggc uguccagaug ua                                              22

<210> SEQ ID NO 126
<211> LENGTH: 23
<212> TYPE: RNA
<213> ORGANISM: Homo sapiens

<400> SEQUENCE: 126
```
agguuguccg uggugaguuc gca                                               23

<210> SEQ ID NO 127
<211> LENGTH: 21
<212> TYPE: RNA
<213> ORGANISM: Homo sapiens

<400> SEQUENCE: 127
ucgaggagcu cacagucuag u                                                 21

<210> SEQ ID NO 128
<211> LENGTH: 22
<212> TYPE: RNA
<213> ORGANISM: Homo sapiens

<400> SEQUENCE: 128
uggcaguguc uuagcugguu gu                                                22

<210> SEQ ID NO 129
<211> LENGTH: 22
<212> TYPE: RNA
<213> ORGANISM: Homo sapiens

<400> SEQUENCE: 129
gcugacuccu aguccagggc uc                                                22

<210> SEQ ID NO 130
<211> LENGTH: 23
<212> TYPE: RNA
<213> ORGANISM: Homo sapiens

<400> SEQUENCE: 130
ucuggcuccg ugucuucacu ccc                                               23

<210> SEQ ID NO 131
<211> LENGTH: 78
<212> TYPE: DNA
<213> ORGANISM: Homo sapiens

<400> SEQUENCE: 131
ctgaggagca gggcttagct gcttgtgagc agggtccaca ccaagtcgtg ttcacagtgg       60
ctaagttccg cccccccag                                                    78

<210> SEQ ID NO 132
<211> LENGTH: 99
<212> TYPE: DNA
<213> ORGANISM: Homo sapiens

<400> SEQUENCE: 132
ccgatgtgta tcctcagctt tgagaactga attccatggg ttgtgtcagt gtcagacctc       60
tgaaattcag ttcttcagct gggatatctc tgtcatcgt                              99

<210> SEQ ID NO 133
<211> LENGTH: 21
<212> TYPE: RNA
<213> ORGANISM: Homo sapiens

<400> SEQUENCE: 133
cuauacaauc uacugucuuu c                                                 21

<210> SEQ ID NO 134
<211> LENGTH: 22

```
<212> TYPE: RNA
<213> ORGANISM: Homo sapiens

<400> SEQUENCE: 134
ugagguagua gguugugugg uu                                            22

<210> SEQ ID NO 135
<211> LENGTH: 22
<212> TYPE: RNA
<213> ORGANISM: Homo sapiens

<400> SEQUENCE: 135
cuauacaacc uacugccuuc cc                                            22

<210> SEQ ID NO 136
<211> LENGTH: 22
<212> TYPE: RNA
<213> ORGANISM: Homo sapiens

<400> SEQUENCE: 136
ugagguagua gguuguaugg uu                                            22

<210> SEQ ID NO 137
<211> LENGTH: 22
<212> TYPE: RNA
<213> ORGANISM: Homo sapiens

<400> SEQUENCE: 137
uagaguuaca cccugggagu ua                                            22

<210> SEQ ID NO 138
<211> LENGTH: 22
<212> TYPE: RNA
<213> ORGANISM: Homo sapiens

<400> SEQUENCE: 138
agagguagua gguugcauag uu                                            22

<210> SEQ ID NO 139
<211> LENGTH: 22
<212> TYPE: RNA
<213> ORGANISM: Homo sapiens

<400> SEQUENCE: 139
cuauacgacc ugcugccuuu cu                                            22

<210> SEQ ID NO 140
<211> LENGTH: 22
<212> TYPE: RNA
<213> ORGANISM: Homo sapiens

<400> SEQUENCE: 140
ugagguagga gguuguauag uu                                            22

<210> SEQ ID NO 141
<211> LENGTH: 22
<212> TYPE: RNA
<213> ORGANISM: Homo sapiens

<400> SEQUENCE: 141
cuauacggcc uccuagcuuu cc                                            22

<210> SEQ ID NO 142
```

```
<211> LENGTH: 22
<212> TYPE: RNA
<213> ORGANISM: Homo sapiens

<400> SEQUENCE: 142
ugagguagua gauuguauag uu                                              22

<210> SEQ ID NO 143
<211> LENGTH: 22
<212> TYPE: RNA
<213> ORGANISM: Homo sapiens

<400> SEQUENCE: 143
cuauacaauc uauugccuuc cc                                              22

<210> SEQ ID NO 144
<211> LENGTH: 22
<212> TYPE: RNA
<213> ORGANISM: Homo sapiens

<400> SEQUENCE: 144
cuauacaguc uacugucuuu cc                                              22

<210> SEQ ID NO 145
<211> LENGTH: 22
<212> TYPE: RNA
<213> ORGANISM: Homo sapiens

<400> SEQUENCE: 145
ugagguagua guuuguacag uu                                              22

<210> SEQ ID NO 146
<211> LENGTH: 21
<212> TYPE: RNA
<213> ORGANISM: Homo sapiens

<400> SEQUENCE: 146
cuguacaggc cacugccuug c                                               21

<210> SEQ ID NO 147
<211> LENGTH: 22
<212> TYPE: RNA
<213> ORGANISM: Homo sapiens

<400> SEQUENCE: 147
ugagguagua guuugugcug uu                                              22

<210> SEQ ID NO 148
<211> LENGTH: 22
<212> TYPE: RNA
<213> ORGANISM: Homo sapiens

<400> SEQUENCE: 148
cugcgcaagc uacugccuug cu                                              22

<210> SEQ ID NO 149
<211> LENGTH: 23
<212> TYPE: RNA
<213> ORGANISM: Homo sapiens

<400> SEQUENCE: 149 agugggaac ccuuccauga gga                                              23
```

```
<210> SEQ ID NO 150
<211> LENGTH: 24
<212> TYPE: RNA
<213> ORGANISM: Homo sapiens

<400> SEQUENCE: 150
guccaguuuu cccaggaauc ccuu                                         24

<210> SEQ ID NO 151
<211> LENGTH: 23
<212> TYPE: RNA
<213> ORGANISM: Homo sapiens

<400> SEQUENCE: 151
cccaguguuc agacuaccug uuc                                          23

<210> SEQ ID NO 152
<211> LENGTH: 22
<212> TYPE: RNA
<213> ORGANISM: Homo sapiens

<400> SEQUENCE: 152
uaacacuguc ugguaaagau gg                                           22

<210> SEQ ID NO 153
<211> LENGTH: 22
<212> TYPE: RNA
<213> ORGANISM: Homo sapiens

<400> SEQUENCE: 153
uggcagugua uuguuagcug gu                                           22

<210> SEQ ID NO 154
<211> LENGTH: 23
<212> TYPE: RNA
<213> ORGANISM: Homo sapiens

<400> SEQUENCE: 154
uggcaguguc uuagcugguu guu                                          23

<210> SEQ ID NO 155
<211> LENGTH: 22
<212> TYPE: RNA
<213> ORGANISM: Homo sapiens

<400> SEQUENCE: 155
uagcagcacg uaaauauugg cg                                           22

<210> SEQ ID NO 156
<211> LENGTH: 21
<212> TYPE: RNA
<213> ORGANISM: Homo sapiens

<400> SEQUENCE: 156
cagcagcaca cugugguuug u                                            21

<210> SEQ ID NO 157
<211> LENGTH: 22
<212> TYPE: RNA
<213> ORGANISM: Homo sapiens

<400> SEQUENCE: 157
uagcagcaca ucaugguuua ca                                           22
```

```
<210> SEQ ID NO 158
<211> LENGTH: 23
<212> TYPE: RNA
<213> ORGANISM: Homo sapiens

<400> SEQUENCE: 158
agcagcauug uacagggcua uca                                          23

<210> SEQ ID NO 159
<211> LENGTH: 23
<212> TYPE: RNA
<213> ORGANISM: Homo sapiens

<400> SEQUENCE: 159
agcagcauug uacagggcua uga                                          23

<210> SEQ ID NO 160
<211> LENGTH: 23
<212> TYPE: RNA
<213> ORGANISM: Homo sapiens

<400> SEQUENCE: 160
aaaagcuggg uugagagggc gaa                                          23

<210> SEQ ID NO 161
<211> LENGTH: 22
<212> TYPE: RNA
<213> ORGANISM: Homo sapiens

<400> SEQUENCE: 161
cuacaaaggg aagcacuuuc uc                                           22

<210> SEQ ID NO 162
<211> LENGTH: 22
<212> TYPE: RNA
<213> ORGANISM: Homo sapiens

<400> SEQUENCE: 162
auaaagcuag auaaccgaaa gu                                           22

<210> SEQ ID NO 163
<211> LENGTH: 18
<212> TYPE: RNA
<213> ORGANISM: Homo sapiens

<400> SEQUENCE: 163
ugcuuccuuu cagagggu                                                18

<210> SEQ ID NO 164
<211> LENGTH: 23
<212> TYPE: RNA
<213> ORGANISM: Homo sapiens

<400> SEQUENCE: 164
gcaaagcaca cggccugcag aga                                          23

<210> SEQ ID NO 165
<211> LENGTH: 20
<212> TYPE: RNA
<213> ORGANISM: Homo sapiens

<400> SEQUENCE: 165
cuacaaaggg aagcccuuuc                                              20
```

<210> SEQ ID NO 166
<211> LENGTH: 21
<212> TYPE: RNA
<213> ORGANISM: Homo sapiens

<400> SEQUENCE: 166
aacuggccua caaagucccca g                                              21

<210> SEQ ID NO 167
<211> LENGTH: 21
<212> TYPE: RNA
<213> ORGANISM: Homo sapiens

<400> SEQUENCE: 167
uauugcacuu gucccggccu g                                               21

<210> SEQ ID NO 168
<211> LENGTH: 22
<212> TYPE: RNA
<213> ORGANISM: Homo sapiens

<400> SEQUENCE: 168
aacauucaac cugucgguga gu                                              22

<210> SEQ ID NO 169
<211> LENGTH: 24
<212> TYPE: RNA
<213> ORGANISM: Homo sapiens

<400> SEQUENCE: 169
ugaaacauac acgggaaacc ucuu                                            24

<210> SEQ ID NO 170
<211> LENGTH: 23
<212> TYPE: RNA
<213> ORGANISM: Homo sapiens

<400> SEQUENCE: 170 cgcaucccccu agggcauugg ugu                                            23

<210> SEQ ID NO 171
<211> LENGTH: 22
<212> TYPE: RNA
<213> ORGANISM: Homo sapiens

<400> SEQUENCE: 171
uaauacugcc ggguaaugau gg                                              22

<210> SEQ ID NO 172
<211> LENGTH: 23
<212> TYPE: RNA
<213> ORGANISM: Homo sapiens

<400> SEQUENCE: 172
uaauacugcc ugguaaugau gac                                             23

<210> SEQ ID NO 173
<211> LENGTH: 20
<212> TYPE: RNA
<213> ORGANISM: Homo sapiens

<400> SEQUENCE: 173
uguaaacauc cuugacugga                                                  20

<210> SEQ ID NO 174
<211> LENGTH: 21
<212> TYPE: RNA
<213> ORGANISM: Homo sapiens

<400> SEQUENCE: 174
uaaagugcug acagugcaga u                                                21

<210> SEQ ID NO 175
<211> LENGTH: 24
<212> TYPE: RNA
<213> ORGANISM: Homo sapiens

<400> SEQUENCE: 175
aaaagugcuu acagugcagg uagc                                             24

<210> SEQ ID NO 176
<211> LENGTH: 21
<212> TYPE: RNA
<213> ORGANISM: Homo sapiens

<400> SEQUENCE: 176
uggaauguaa agaaguaugu a                                                21

<210> SEQ ID NO 177
<211> LENGTH: 23
<212> TYPE: RNA
<213> ORGANISM: Homo sapiens

<400> SEQUENCE: 177
ucccugagac ccuuuaaccu gug                                              23

<210> SEQ ID NO 178
<211> LENGTH: 22
<212> TYPE: RNA
<213> ORGANISM: Homo sapiens

<400> SEQUENCE: 178
ucccugagac ccuaacuugu ga                                               22

<210> SEQ ID NO 179
<211> LENGTH: 21
<212> TYPE: RNA
<213> ORGANISM: Homo sapiens

<400> SEQUENCE: 179
aucgggaaug ucguguccgc c                                                21

<210> SEQ ID NO 180
<211> LENGTH: 23
<212> TYPE: RNA
<213> ORGANISM: Homo sapiens

<400> SEQUENCE: 180
uaaagugcuu auagugcagg uag                                              23

<210> SEQ ID NO 181
<211> LENGTH: 24
<212> TYPE: RNA
<213> ORGANISM: Homo sapiens

<400> SEQUENCE: 181

```
caaagugcuu acagugcagg uagu                                          24

<210> SEQ ID NO 182
<211> LENGTH: 22
<212> TYPE: RNA
<213> ORGANISM: Homo sapiens

<400> SEQUENCE: 182
aaagugcugu ucgugcaggu ag                                            22

<210> SEQ ID NO 183
<211> LENGTH: 21
<212> TYPE: RNA
<213> ORGANISM: Homo sapiens

<400> SEQUENCE: 183
uauugcacuc gucccggccu c                                             21

<210> SEQ ID NO 184
<211> LENGTH: 21
<212> TYPE: RNA
<213> ORGANISM: Homo sapiens

<400> SEQUENCE: 184
uauugcacau uacuaaguug c                                             21

<210> SEQ ID NO 185
<211> LENGTH: 20
<212> TYPE: RNA
<213> ORGANISM: Homo sapiens

<400> SEQUENCE: 185
ccucugggcc cuuccuccag                                               20

<210> SEQ ID NO 186
<211> LENGTH: 23
<212> TYPE: RNA
<213> ORGANISM: Homo sapiens

<400> SEQUENCE: 186
ucaaaugcuc agacuccugu ggu                                           23

<210> SEQ ID NO 187
<211> LENGTH: 23
<212> TYPE: RNA
<213> ORGANISM: Homo sapiens

<400> SEQUENCE: 187
caacggaauc ccaaaagcag cug                                           23

<210> SEQ ID NO 188
<211> LENGTH: 21
<212> TYPE: RNA
<213> ORGANISM: Homo sapiens

<400> SEQUENCE: 188
cacgcucaug cacacaccca c                                             21

<210> SEQ ID NO 189
<211> LENGTH: 23
<212> TYPE: RNA
<213> ORGANISM: Homo sapiens
```

```
<400> SEQUENCE: 189
caaagaauuc uccuuuuggg cuu                                    23

<210> SEQ ID NO 190
<211> LENGTH: 23
<212> TYPE: RNA
<213> ORGANISM: Homo sapiens

<400> SEQUENCE: 190
uagcaccauu ugaaaucagu guu                                    23

<210> SEQ ID NO 191
<211> LENGTH: 21
<212> TYPE: RNA
<213> ORGANISM: Homo sapiens

<400> SEQUENCE: 191
uagcaccauc ugaaaucggu u                                      21

<210> SEQ ID NO 192
<211> LENGTH: 20
<212> TYPE: RNA
<213> ORGANISM: Homo sapiens

<400> SEQUENCE: 192
uagcaccauu ugaaaucggu                                        20

<210> SEQ ID NO 193
<211> LENGTH: 22
<212> TYPE: RNA
<213> ORGANISM: Homo sapiens

<400> SEQUENCE: 193
acuagacuga agcuccuuga gg                                     22

<210> SEQ ID NO 194
<211> LENGTH: 21
<212> TYPE: RNA
<213> ORGANISM: Homo sapiens

<400> SEQUENCE: 194
uagguaguuu cauguuguug g                                      21

<210> SEQ ID NO 195
<211> LENGTH: 21
<212> TYPE: RNA
<213> ORGANISM: Homo sapiens

<400> SEQUENCE: 195
agugguuuua cccuauggua g                                      21

<210> SEQ ID NO 196
<211> LENGTH: 22
<212> TYPE: RNA
<213> ORGANISM: Homo sapiens

<400> SEQUENCE: 196
agcucggucu gaggccccuc ag                                     22

<210> SEQ ID NO 197
<211> LENGTH: 22
<212> TYPE: RNA
<213> ORGANISM: Homo sapiens
```

```
<400> SEQUENCE: 197
agggcuuagc ugcuugugag ca                                          22

<210> SEQ ID NO 198
<211> LENGTH: 22
<212> TYPE: RNA
<213> ORGANISM: Homo sapiens

<400> SEQUENCE: 198
ugagaacuga auuccauggg uu                                          22

<210> SEQ ID NO 199
<211> LENGTH: 22
<212> TYPE: RNA
<213> ORGANISM: Homo sapiens

<400> SEQUENCE: 199
ccucugaaau ucaguucuuc ag                                          22
```